(12) United States Patent
Fukui et al.

(10) Patent No.: US 8,628,941 B2
(45) Date of Patent: Jan. 14, 2014

(54) L-AMINO ACID-PRODUCING BACTERIUM AND A METHOD FOR PRODUCING L-AMINO ACID

(75) Inventors: Keita Fukui, Kawasaki (JP); Jun Nakamura, Kawasaki (JP); Hiroyuki Kojima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1264 days.

(21) Appl. No.: 11/753,710

(22) Filed: May 25, 2007

(65) Prior Publication Data

US 2007/0254345 A1 Nov. 1, 2007

Related U.S. Application Data

(63) Continuation of application No. PCT/JP2005/022137, filed on Nov. 25, 2005.

(30) Foreign Application Priority Data

Nov. 25, 2004 (JP) .................................. 2004-340187

(51) Int. Cl.
C12P 13/14 (2006.01)

(52) U.S. Cl.
USPC ..................... 435/110; 435/252.32; 435/116

(58) Field of Classification Search
None
See application file for complete search history.

(56) References Cited

U.S. PATENT DOCUMENTS

| | | | |
|---|---|---|---|
| 5,143,833 | A | 9/1992 | Datta |
| 5,504,004 | A | 4/1996 | Guettler et al. |
| 7,090,998 | B2 | 8/2006 | Ishikawa et al. |
| 7,205,132 | B2 | 4/2007 | Hirano et al. |
| 7,332,310 | B2 * | 2/2008 | Nakagawa et al. ........... 435/115 |
| 2004/0002143 | A1 | 1/2004 | Asakura et al. |
| 2004/0152175 | A1 | 8/2004 | Nakamura et al. |
| 2004/0265956 | A1 | 12/2004 | Takikawa et al. |
| 2005/0014236 | A1 | 1/2005 | Matsuzaki et al. |
| 2005/0196848 | A1 | 9/2005 | Dusch et al. |
| 2006/0141588 | A1 | 6/2006 | Nakamura et al. |

FOREIGN PATENT DOCUMENTS

| | | |
|---|---|---|
| EP | 1096013 | 5/2001 |
| EP | 1 108 790 | 6/2001 |
| JP | 06-014781 | 1/1994 |
| JP | 07-067683 | 3/1995 |
| JP | 11-113588 | 4/1999 |
| JP | 11-196888 | 7/1999 |
| JP | 11-206385 | 8/1999 |
| WO | WO99/06532 | 2/1999 |
| WO | WO00/18935 | 4/2000 |
| WO | WO02/29020 | 4/2002 |
| WO | WO02/36797 | 5/2002 |
| WO | WO02/072855 | 9/2002 |
| WO | WO03/040290 | 5/2003 |
| WO | WO2006/057450 | 6/2006 |

OTHER PUBLICATIONS

Wells, Biochemistry, vol. 29, pp. 8509-8517, 1990.*
Hermann, T., "Industrial production of amino acids by Coryneform bacteria," J. Biotechnol. 2003;104:155-172.
Kalinowski, J., et al., "The complete *Coryneform glutamicum* ATCC 13032 genome sequence and its impact on the production of L-aspartate-derived amino acids and vitamins," J. Biotechnol. 2003;104:5-25.
Kirchner, O., et al., "Tools for genetic engineering in the amino acid-producing bacterium *Corynebacterium glutamicum*," J. Biotechnol. 2003;104:287-299.
International Search Report for PCT Patent App. No. PCT/JP2005/022137 (Mar. 24, 2006).
International Preliminary Report on Patentability for PCT Patent App. No. PCT/JP2005/022137 (Jun. 7, 2007).
Guettler, M. V., et al., "*Actinobacillus succinogenes* sp. nov., a novel succinic-acid-producing strain from the bovine rumen," Int. J. Sys. Bacteriol. 1999;49:207-216.
Reinscheid, D. J., et al., "Cloning, sequence analysis, expression and inactivation of the *Corynebacterium glutamicum* pta-ack operon encoding phosphotransacetylase and acetate kinase," Microbiol. 1999;145:503-513.
U.S. Appl. No. 09/307,450, filed May 10, 1999, Kojima et al.
U.S. Appl. No. 09/495,310, filed Feb. 1, 2000, Kojima et al.
U.S. Appl. No. 10/149,450, filed Jun. 27, 2002, Nakanishi et al.
U.S. Appl. No. 60/641,079, filed Jan. 4, 2005, Nakamura et al.
U.S. Appl. No. 60/641,080, filed Jan. 4, 2005, Nakamura et al.
U.S. Appl. No. 60/651,229, filed Feb. 10, 2005, Hirano et al.
U.S. Appl. No. 60/715,131, filed Sep. 9, 2005, Nakamura et al.
U.S. Appl. No. 11/682,370, filed Mar. 6, 2007, Hirano et al.
Notice of Reason for Rejection for Japanese Patent App. No. 2004-340187 (Jun. 15, 2010) with English translation thereof.

* cited by examiner

*Primary Examiner* — Hope Robinson

(74) *Attorney, Agent, or Firm* — Shelly Guest Cermak; Cermak Nakajima LLP

(57) ABSTRACT

Coryneform bacteria are described that have an ability to produce L-amino acids and are modified so that acetyl-CoA hydrolase activity is decreased. The bacteria are used to produce L-amino acids generated by a biosynthetic pathway in which pyruvic acid is an intermediate, such as L-glutamic acid, L-arginine, L-glutamine, L-proline, L-alanine, L-valine, and L-lysine.

6 Claims, 5 Drawing Sheets

SEQUENCE LISTING

<160> NUMBER OF SEQ ID NOS: 26

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
cgggatcctt tttaacccat caca                           24

<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2
gaagatcttc aaaaggttag gaatacggt                      29

<210> SEQ ID NO 3
<211> LENGTH: 23
<212> TYPE: DNA
<213> ORGANISM: Artificial Sequence
<220> FEATURE:
<223> OTHER INFORMATION: primer

<400> SEQUENCE: 3 cctttgaag atcgaccagt tgg                             23

<210> SEQ ID NO 4
<211> LENGTH: 44
<212> TYPE: DNA
<213> ORGANISM: Artificial Sequence
<220> FEATURE:
<223> OTHER INFORMATION: primer

<400> SEQUENCE: 4
tacctggaat gctgttttcc cagggatcgc agtggtgagt aacc     44

<210> SEQ ID NO 5
<211> LENGTH: 28
<212> TYPE: DNA
<213> ORGANISM: Artificial Sequence
<220> FEATURE:
<223> OTHER INFORMATION: primer

<400> SEQUENCE: 5
cctgggaaaa cagcattcca ggtattag                       28

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
tgcaggtcga ctctagagga tcc                            23

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
cactgcacgg ccctgcgaac                                20

<210> SEQ ID NO 8
<211> LENGTH: 42
<212> TYPE: DNA
<213> ORGANISM: Artificial Sequence

```
<220> FEATURE:
<223> OTHER INFORMATION: primer

<400> SEQUENCE: 8
cgccaactag gcgccaaaaa ttcctgattt ccctaaccgg ac                    42

<210> SEQ ID NO 9
<211> LENGTH: 42
<212> TYPE: DNA
<213> ORGANISM: Artificial Sequence
<220> FEATURE:
<223> OTHER INFORMATION: primer

<400> SEQUENCE: 9
gtccggttag ggaaatcagg aattttggc gcctagttgg cg                     42

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tgtgggcctt cggcgaggac                                             20

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
gagtcgaccg caccccattt ttcata                                      26

<210> SEQ ID NO 12
<211> LENGTH: 28
<212> TYPE: DNA
<213> ORGANISM: Artificial Sequence
<220> FEATURE:
<223> OTHER INFORMATION: primer

<400> SEQUENCE: 12
tggtcgacgt gaatgctcgg cgggatcc                                    28

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
gcttctgcgc aaagcaagcc tccg                                        24

<210> SEQ ID NO 14
<211> LENGTH: 50
<212> TYPE: DNA
<213> ORGANISM: Artificial Sequence
<220> FEATURE:
<223> OTHER INFORMATION: primer

<400> SEQUENCE: 14
gtccgattac ctgaggaggt attcccatga aggcataagt ttttcttgg             50
```

-continued

```
<210> SEQ ID NO 15
<211> LENGTH: 50
<212> TYPE: DNA
<213> ORGANISM: Artificial Sequence
<220> FEATURE:
<223> OTHER INFORMATION: primer

<400> SEQUENCE: 15
ccaagaaaaa acttatgcct tcatgggaat acctcctcag gtaatcggac          50

<210> SEQ ID NO 16
<211> LENGTH: 26
<212> TYPE: DNA
<213> ORGANISM: Artificial Sequence
<220> FEATURE:
<223> OTHER INFORMATION: primer

<400> SEQUENCE: 16
ggtcatgtgc atggttttct cattgc                                    26

<210> SEQ ID NO 17
<211> LENGTH: 33
<212> TYPE: DNA
<213> ORGANISM: Artificial Sequence
<220> FEATURE:
<223> OTHER INFORMATION: primer

<400> SEQUENCE: 17
ggcctctaga cctgcaccga tcaggatgag tgg                            33

<210> SEQ ID NO 18
<211> LENGTH: 35
<212> TYPE: DNA
<213> ORGANISM: Artificial Sequence
<220> FEATURE:
<223> OTHER INFORMATION: primer

<400> SEQUENCE: 18
gcgctctaga ctcaacaaga gcacgcgcag tcacc                          35

<210> SEQ ID NO 19
<211> LENGTH: 2014
<212> TYPE: DNA
<213> ORGANISM: Bacillus subtilis
<220> FEATURE:
<221> NAME/KEY: CDS
<222> LOCATION: (464)..(1882)

<400> SEQUENCE: 19
gatccttttt aacccatcac atatacctgc cgttcactat tatttagtga atgagatat   60 tatgatattt tctgaattgt gattaaaaag gcaactttat gcccatgcaa cagaaactat   120
aaaaaataca gagaatgaaa agaaacagat agatttttta gttctttagg cccgtagtct   180
gcaaatcctt ttatgatttt ctatcaaaca aagaggaaa atagaccagt tgcaatccaa   240
acgagagtct aatagaatga ggtcgaaaag taaatcgcgc gggtttgtta ctgataaagc   300
aggcaagacc taaatgtgt aaagggcaaa gtgtatactt tggcgtcacc ccttacatat   360
tttaggtctt ttttattgt gcgtaactaa cttgccatct tcaaacagga gggctggaag   420
aagcagaccg ctaacacagt acataaaaaa ggagacatga acg atg aac atc aaa    475
                                              Met Asn Ile Lys
                                              1 aag ttt gca aaa caa gca aca gta tta acc ttt act acc gca ctg ctg    523
Lys Phe Ala Lys Gln Ala Thr Val Leu Thr Phe Thr Thr Ala Leu Leu
 5                  10                  15                  20
```

-continued

```
gca gga ggc gca act caa gcg ttt gcg aaa gaa acg aac caa aag cca    571
Ala Gly Gly Ala Thr Gln Ala Phe Ala Lys Glu Thr Asn Gln Lys Pro
             25                  30                  35 tat aag gaa aca tac ggc att tcc cat att aca cgc cat gat atg ctg    619
Tyr Lys Glu Thr Tyr Gly Ile Ser His Ile Thr Arg His Asp Met Leu
         40                  45                  50 caa atc cct gaa cag caa aaa aat gaa aaa tat caa gtt cct gaa ttc    667
Gln Ile Pro Glu Gln Gln Lys Asn Glu Lys Tyr Gln Val Pro Glu Phe
         55                  60                  65 gat tcg tcc aca att aaa aat atc tct tct gca aaa ggc ctg gac gtt    715
Asp Ser Ser Thr Ile Lys Asn Ile Ser Ser Ala Lys Gly Leu Asp Val
     70                  75                  80 tgg gac agc tgg cca tta caa aac gct gac ggc act gtc gca aac tat    763
Trp Asp Ser Trp Pro Leu Gln Asn Ala Asp Gly Thr Val Ala Asn Tyr
85                  90                  95                 100 cac ggc tac cac atc gtc ttt gca tta gcc gga gat cct aaa aat gcg    811
His Gly Tyr His Ile Val Phe Ala Leu Ala Gly Asp Pro Lys Asn Ala
             105                 110                 115 gat gac aca tcg att tac atg ttc tat caa aaa gtc ggc gaa act tct    859
Asp Asp Thr Ser Ile Tyr Met Phe Tyr Gln Lys Val Gly Glu Thr Ser
         120                 125                 130 att gac agc tgg aaa aac gct ggc cgc gtc ttt aaa gac agc gac aaa    907
Ile Asp Ser Trp Lys Asn Ala Gly Arg Val Phe Lys Asp Ser Asp Lys
         135                 140                 145 ttc gat gca aat gat tct atc cta aaa gac caa aca caa gaa tgg tca    955
Phe Asp Ala Asn Asp Ser Ile Leu Lys Asp Gln Thr Gln Glu Trp Ser
     150                 155                 160 ggt tca gcc aca ttt aca tct gac gga aaa atc cgt tta ttc tac act    1003
Gly Ser Ala Thr Phe Thr Ser Asp Gly Lys Ile Arg Leu Phe Tyr Thr
165                 170                 175                 180 gat ttc tcc ggt aaa cat tac ggc aaa caa aca ctg aca act gca caa    1051
Asp Phe Ser Gly Lys His Tyr Gly Lys Gln Thr Leu Thr Thr Ala Gln
             185                 190                 195 gtt aac gta tca gca tca gac agc tct ttg aac atc aac ggt gta gag    1099
Val Asn Val Ser Ala Ser Asp Ser Ser Leu Asn Ile Asn Gly Val Glu
         200                 205                 210 gat tat aaa tca atc ttt gac ggt gac gga aaa acg tat caa aat gta    1147
Asp Tyr Lys Ser Ile Phe Asp Gly Asp Gly Lys Thr Tyr Gln Asn Val
         215                 220                 225 cag cag ttc atc gat gaa ggc aac tac agc tca ggc gac aac cat acg    1195
Gln Gln Phe Ile Asp Glu Gly Asn Tyr Ser Ser Gly Asp Asn His Thr
     230                 235                 240 ctg aga gat cct cac tac gta gaa gat aaa ggc cac aaa tac tta gta    1243
Leu Arg Asp Pro His Tyr Val Glu Asp Lys Gly His Lys Tyr Leu Val
245                 250                 255                 260 ttt gaa gca aac act gga act gaa gat ggc tac caa ggc gaa gaa tct    1291
Phe Glu Ala Asn Thr Gly Thr Glu Asp Gly Tyr Gln Gly Glu Glu Ser
             265                 270                 275 tta ttt aac aaa gca tac tat ggc aaa agc aca tca ttc ttc cgt caa    1339
Leu Phe Asn Lys Ala Tyr Tyr Gly Lys Ser Thr Ser Phe Phe Arg Gln
         280                 285                 290 gaa agt caa aaa ctt ctg caa agc gat aaa aaa cgc acg gct gag tta    1387
Glu Ser Gln Lys Leu Leu Gln Ser Asp Lys Lys Arg Thr Ala Glu Leu
         295                 300                 305 gca aac ggc gct ctc ggt atg att gag cta aac gat gat tac aca ctg    1435
Ala Asn Gly Ala Leu Gly Met Ile Glu Leu Asn Asp Asp Tyr Thr Leu
     310                 315                 320 aaa aaa gtg atg aaa ccg ctg att gca tct aac aca gta aca gat gaa    1483
Lys Lys Val Met Lys Pro Leu Ile Ala Ser Asn Thr Val Thr Asp Glu
325                 330                 335                 340
```

```
att gaa cgc gcg aac gtc ttt aaa atg aac ggc aaa tgg tac ctg ttc    1531
Ile Glu Arg Ala Asn Val Phe Lys Met Asn Gly Lys Trp Tyr Leu Phe
            345                 350                 355 act gac tcc cgc gga tca aaa atg acg att gac ggc att acg tct aac    1579
Thr Asp Ser Arg Gly Ser Lys Met Thr Ile Asp Gly Ile Thr Ser Asn
        360                 365                 370 gat att tac atg ctt ggt tat gtt tct aat tct tta act ggc cca tac    1627
Asp Ile Tyr Met Leu Gly Tyr Val Ser Asn Ser Leu Thr Gly Pro Tyr
    375                 380                 385 aag ccg ctg aac aaa act ggc ctt gtg tta aaa atg gat ctt gat cct    1675
Lys Pro Leu Asn Lys Thr Gly Leu Val Leu Lys Met Asp Leu Asp Pro
390                 395                 400 aac gat gta acc ttt act tac tca cac ttc gct gta cct caa gcg aaa    1723
Asn Asp Val Thr Phe Thr Tyr Ser His Phe Ala Val Pro Gln Ala Lys
405                 410                 415                 420 gga aac aat gtc gtg att aca agc tat atg aca aac aga gga ttc tac    1771
Gly Asn Asn Val Val Ile Thr Ser Tyr Met Thr Asn Arg Gly Phe Tyr
                425                 430                 435 gca gac aaa caa tca acg ttt gcg cca agc ttc ctg ctg aac atc aaa    1819
Ala Asp Lys Gln Ser Thr Phe Ala Pro Ser Phe Leu Leu Asn Ile Lys
            440                 445                 450 ggc aag aaa aca tct gtt gtc aaa gac agc atc ctt gaa caa gga caa    1867
Gly Lys Lys Thr Ser Val Val Lys Asp Ser Ile Leu Glu Gln Gly Gln
        455                 460                 465 tta aca gtt aac aaa taa aaacgcaaaa gaaaatgccg atatcctatt           1915
Leu Thr Val Asn Lys
    470 ggcattttct tttatttctt atcaacataa aggtgaatcc catatgaact atataaaagc  1975 aggcaaatgg ctaaccgtat tcctaacctt ttgaagatc                         2014

<210> SEQ ID NO 20
<211> LENGTH: 473
<212> TYPE: PRT
<213> ORGANISM: Bacillus subtilis

<400> SEQUENCE: 20

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

His Asp Met Leu Gln Ile Pro Glu Gln Gln Lys Asn Glu Lys Tyr Gln
    50                  55                  60

Val Pro Glu Phe Asp Ser Ser Thr Ile Lys Asn Ile Ser Ser Ala Lys
65                  70                  75                  80

Gly Leu Asp Val Trp Asp Ser Trp Pro Leu Gln Asn Ala Asp Gly Thr
                85                  90                  95

Val Ala Asn Tyr His Gly Tyr His Ile Val Phe Ala Leu Ala Gly Asp
            100                 105                 110

Pro Lys Asn Ala Asp Asp Thr Ser Ile Tyr Met Phe Tyr Gln Lys Val
        115                 120                 125

Gly Glu Thr Ser Ile Asp Ser Trp Lys Asn Ala Gly Arg Val Phe Lys
    130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175
```

```
Leu Phe Tyr Thr Asp Phe Ser Gly Lys His Tyr Gly Lys Gln Thr Leu
            180                 185                 190

Thr Thr Ala Gln Val Asn Val Ser Ala Ser Asp Ser Leu Asn Ile
        195                 200                 205

Asn Gly Val Glu Asp Tyr Lys Ser Ile Phe Asp Gly Asp Gly Lys Thr
        210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
                260                 265                 270

Gly Glu Glu Ser Leu Phe Asn Lys Ala Tyr Tyr Gly Lys Ser Thr Ser
            275                 280                 285

Phe Phe Arg Gln Glu Ser Gln Lys Leu Leu Gln Ser Asp Lys Lys Arg
        290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
            340                 345                 350

Trp Tyr Leu Phe Thr Asp Ser Arg Gly Ser Lys Met Thr Ile Asp Gly
        355                 360                 365

Ile Thr Ser Asn Asp Ile Tyr Met Leu Gly Tyr Val Ser Asn Ser Leu
        370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
                420                 425                 430

Arg Gly Phe Tyr Ala Asp Lys Gln Ser Thr Phe Ala Pro Ser Phe Leu
        435                 440                 445

Leu Asn Ile Lys Gly Lys Lys Thr Ser Val Val Lys Asp Ser Ile Leu
        450                 455                 460

Glu Gln Gly Gln Leu Thr Val Asn Lys
465                 470

<210> SEQ ID NO 21
<211> LENGTH: 2820
<212> TYPE: DNA
<213> ORGANISM: Corynebacterium glutamicum
<220> FEATURE:
<221> NAME/KEY: CDS
<222> LOCATION: (898)..(1851)

<400> SEQUENCE: 21
tgcagaatta tgcaagatgc gccgcaacaa aacgcgatcg gccaaggtca aagtggtcaa      60
tgtaatgacc gaaaccgctg cgatgaaact tatccacggc ggtaaaaacc tctcaattag    120
gagcttgacc tcattaatac tgtgctgggt taattcgccg gtgatcagca gcgcgccgta    180
ccccaaggtg ccgacactaa tgcccgcgat cgtctccttc ggtccaaaat tcttctgccc    240
aatcagccgg atttgggtgc gatgcctgat caatcccaca accgtggtgg tcaacgtgat    300
ggcaccagtt gcgatgtggg tggcgttgta aattttcctg ataccggcc ggttggttct    360
```

```
ggggaggatc gagtggattc cgtcgctgc cgcatgcccc accgcttgta aaacagccag      420
gttagcagcc gtaacccacc acggtttcgg caacaatgac ggcgagagag cccaccacat      480
tgcgatttcc gctccgataa agccagcgcc catatttgca gggaggattc gcctgcggtt      540
tggcgacatt cggatccccg gaactagctc tgcaatgacc tgcgcgccga gggaggcgag      600
gtgggtggca ggttttagtg cgggtttaag cgttgccagg cgagtggtga gcagagacgc      660
tagtctgggg agcgaaacca tattgagtca tcttggcaga gcatgcacaa ttctgcaggg      720
cataggttgg ttttgctcga tttacaatgt gattttttca acaaaaataa cacttggtct      780
gaccacattt tcggacataa tcgggcataa ttaaaggtgt aacaaaggaa tccgggcaca      840
agctcttgct gattttctga gctgctttgt gggttgtccg gttagggaaa tcaggaa        897
```

```
gtg gga tcg aaa atg aaa gaa acc gtc ggt aac aag att gtc ctc att        945
Val Gly Ser Lys Met Lys Glu Thr Val Gly Asn Lys Ile Val Leu Ile
1               5                   10                  15 ggc gca gga gat gtt gga gtt gca tac gca tac gca ctg atc aac cag        993
Gly Ala Gly Asp Val Gly Val Ala Tyr Ala Tyr Ala Leu Ile Asn Gln
                20                  25                  30 ggc atg gca gat cac ctt gcg atc atc gac atc gat gaa aag aaa ctc       1041
Gly Met Ala Asp His Leu Ala Ile Ile Asp Ile Asp Glu Lys Lys Leu
            35                  40                  45 gaa ggc aac gtc atg gac tta aac cat ggt gtt gtg tgg gcc gat tcc       1089
Glu Gly Asn Val Met Asp Leu Asn His Gly Val Val Trp Ala Asp Ser
50                  55                  60 cgc acc cgc gtc acc aag ggc acc tac gct gac tgc gaa gac gca gcc       1137
Arg Thr Arg Val Thr Lys Gly Thr Tyr Ala Asp Cys Glu Asp Ala Ala
65                  70                  75                  80 atg gtt gtc att tgt gcc ggc gca gcc caa aag cca ggc gag acc cgc       1185
Met Val Val Ile Cys Ala Gly Ala Ala Gln Lys Pro Gly Glu Thr Arg
                85                  90                  95 ctc cag ctg gtg gac aaa aac gtc aag att atg aaa tcc atc gtc ggc       1233
Leu Gln Leu Val Asp Lys Asn Val Lys Ile Met Lys Ser Ile Val Gly
            100                 105                 110 gat gtc atg gac agc gga ttc gac ggc atc ttc ctc gtg gcg tcc aac       1281
Asp Val Met Asp Ser Gly Phe Asp Gly Ile Phe Leu Val Ala Ser Asn
        115                 120                 125 cca gtg gat atc ctg acc tac gca gtg tgg aaa ttc tcc ggc ttg gaa       1329
Pro Val Asp Ile Leu Thr Tyr Ala Val Trp Lys Phe Ser Gly Leu Glu
130                 135                 140 tgg aac cgc gtg atc ggc tcc gga act gtc ctg gac tcc gct cga ttc       1377
Trp Asn Arg Val Ile Gly Ser Gly Thr Val Leu Asp Ser Ala Arg Phe
145                 150                 155                 160 cgc tac atg ctg ggc gaa ctc tac gaa gtg gca cca agc tcc gtc cac       1425
Arg Tyr Met Leu Gly Glu Leu Tyr Glu Val Ala Pro Ser Ser Val His
                165                 170                 175 gcc tac atc atc ggc gaa cac ggc gac act gaa ctt cca gtc ctg tcc       1473
Ala Tyr Ile Ile Gly Glu His Gly Asp Thr Glu Leu Pro Val Leu Ser
            180                 185                 190 tcc gcg acc atc gca ggc gta tcg ctt agc cga atg ctg gac aaa gac       1521
Ser Ala Thr Ile Ala Gly Val Ser Leu Ser Arg Met Leu Asp Lys Asp
        195                 200                 205 cca gag ctt gag ggc cgt cta gag aaa att ttc gaa gac acc cgc gac       1569
Pro Glu Leu Glu Gly Arg Leu Glu Lys Ile Phe Glu Asp Thr Arg Asp
210                 215                 220 gct gcc tat cac att atc gac gcc aag ggc tcc act tcc tac ggc atc       1617
Ala Ala Tyr His Ile Ile Asp Ala Lys Gly Ser Thr Ser Tyr Gly Ile
225                 230                 235                 240 ggc atg ggt ctt gct cgc atc acc cgc gca atc ctg cag aac caa gac       1665
Gly Met Gly Leu Ala Arg Ile Thr Arg Ala Ile Leu Gln Asn Gln Asp
```

```
Gly Met Gly Leu Ala Arg Ile Thr Arg Ala Ile Leu Gln Asn Gln Asp
            245                 250                 255 gtt gca gtc cca gtc tct gca ctg ctc cac ggt gaa tac ggt gag gaa      1713
Val Ala Val Pro Val Ser Ala Leu Leu His Gly Glu Tyr Gly Glu Glu
            260                 265                 270 gac atc tac atc ggc acc cca gct gtg gtg aac cgc cga ggc atc cgc      1761
Asp Ile Tyr Ile Gly Thr Pro Ala Val Val Asn Arg Arg Gly Ile Arg
            275                 280                 285 cgc gtt gtc gaa cta gaa atc acc gac cac gag atg gaa cgc ttc aag      1809
Arg Val Val Glu Leu Glu Ile Thr Asp His Glu Met Glu Arg Phe Lys
            290                 295                 300 cat tcc gca aat acc ctg cgc gaa att cag aag cag ttc ttc taa          1854
His Ser Ala Asn Thr Leu Arg Glu Ile Gln Lys Gln Phe Phe
305                 310                 315 atctttggcg cctagttggc gacgcaagtg tttcattgga acacttgcgc tgccaacttt    1914
ttggtttacg ggcacaatga aactgttgga tggaatttag agtgttttgta gcttaaggag   1974 ctcaaatgaa tgagtttgac caggacattc tccaggagat caagactgaa ctcgacgagt    2034
taattctaga acttgatgag gtgacacaaa ctcacagcga ggccatcggg caggtctccc    2094
caacccatta cgttggtgcc cgcaacctca tgcattacgc gcatcttcgc accaaagacc    2154
tccgtggcct gcagcaacgc ctctcctctg tgggagctac ccgcttgact accaccgaac    2214
cagcagtgca ggcccgcctc aaggccgccc gcaatgttat cggagctttc gcaggtgaag    2274
gcccacttta tccacccctca gatgtcgtcg atgccttcga agatgccgat gagattctcg   2334
acgagcacgc cgaaattctc cttggcgaac ccctaccgga tactccatcc tgcatcatgg    2394
tcaccctgcc caccgaagcc gccaccgaca ttgaacttgt ccgtggcttc gccaaaagcg    2454
gcatgaatct agctcgcatc aactgtgcac acgacgatga aaccgtctgg aagcagatga    2514
tcgacaacgt ccacaccgtt gcagaagaag ttggccggga atccgcgtc agcatggacc     2574 tcgccggacc aaaagtacgc accggcgaaa tcgccccagg cgcagaagta ggtcgcgcac    2634
gagtaacccg cgacgaaacc ggaaaagtac tgacgcccgc aaaactgtgg atcaccgccc    2694
acggctccga accagtccca gcccccgaaa gcctgcccgg tcgccccgct ctgccgattg    2754
aagtcacccc agaatggttc gacaaactag aaatcggcag cgtcatcaac gtcccagaca    2814
cccgcg                                                               2820

<210> SEQ ID NO 22
<211> LENGTH: 318
<212> TYPE: PRT
<213> ORGANISM: Corynebacterium glutamicum

<400> SEQUENCE: 22

Met Gly Ser Lys Met Lys Glu Thr Val Gly Asn Lys Ile Val Leu Ile
1               5                  10                  15

Gly Ala Gly Asp Val Gly Val Ala Tyr Ala Tyr Ala Leu Ile Asn Gln
            20                  25                  30

Gly Met Ala Asp His Leu Ala Ile Ile Asp Ile Asp Glu Lys Lys Leu
        35                  40                  45

Glu Gly Asn Val Met Asp Leu Asn His Gly Val Val Trp Ala Asp Ser
    50                  55                  60

Arg Thr Arg Val Thr Lys Gly Thr Tyr Ala Asp Cys Glu Asp Ala Ala
65                  70                  75                  80

Met Val Val Ile Cys Ala Gly Ala Ala Gln Lys Pro Gly Glu Thr Arg
                85                  90                  95

Leu Gln Leu Val Asp Lys Asn Val Lys Ile Met Lys Ser Ile Val Gly
```

```
                        100                 105                 110
Asp Val Met Asp Ser Gly Phe Asp Gly Ile Phe Leu Val Ala Ser Asn
            115                 120                 125

Pro Val Asp Ile Leu Thr Tyr Ala Val Trp Lys Phe Ser Gly Leu Glu
            130                 135                 140

Trp Asn Arg Val Ile Gly Ser Gly Thr Val Leu Asp Ser Ala Arg Phe
145                 150                 155                 160

Arg Tyr Met Leu Gly Glu Leu Tyr Glu Val Ala Pro Ser Ser Val His
                165                 170                 175

Ala Tyr Ile Ile Gly Glu His Gly Asp Thr Glu Leu Pro Val Leu Ser
            180                 185                 190

Ser Ala Thr Ile Ala Gly Val Ser Leu Ser Arg Met Leu Asp Lys Asp
            195                 200                 205

Pro Glu Leu Glu Gly Arg Leu Glu Lys Ile Phe Glu Asp Thr Arg Asp
210                 215                 220

Ala Ala Tyr His Ile Ile Asp Ala Lys Gly Ser Thr Ser Tyr Gly Ile
225                 230                 235                 240

Gly Met Gly Leu Ala Arg Ile Thr Arg Ala Ile Leu Gln Asn Gln Asp
                245                 250                 255

Val Ala Val Pro Val Ser Ala Leu Leu His Gly Glu Tyr Gly Glu Glu
            260                 265                 270

Asp Ile Tyr Ile Gly Thr Pro Ala Val Val Asn Arg Arg Gly Ile Arg
            275                 280                 285

Arg Val Val Glu Leu Glu Ile Thr Asp His Glu Met Glu Arg Phe Lys
290                 295                 300

His Ser Ala Asn Thr Leu Arg Glu Ile Gln Lys Gln Phe Phe
305                 310                 315

<210> SEQ ID NO 23
<211> LENGTH: 3600
<212> TYPE: DNA
<213> ORGANISM: Corynebacterium glutamicum
<220> FEATURE:
<221> NAME/KEY: CDS
<222> LOCATION: (1037)..(2542)

<400> SEQUENCE: 23
gaagcgctac ggacttcgcg ccggcgtcga cagcaatgcg tccagcatcc aagtgagtat      60
ggtgctcatc atcaatacca acgcggaact tcaccgtcac cggaatgtcc gtgccttccg     120
tagccttcac agccgcggaa acgatgtttt caaacaaacg gcgcttgtaa ggaatcgcag     180
aaccgccacc ccggcgcgtg acctttggaa ccgggcagcc aaagttcata tcaatatgat     240
ccgccaagtt ttcatcaacg atcatcttcg ccgcttcgta ggtgtacttc gggtcaaccg     300
tgtacagctg caagcttcgg ggattttcat ccggcgcgaa ggtggtcatg tgcatggttt     360
tctcattgcg ctcaacaaga gcacgcgcag tcaccatttc acagacgtac agccccgaga     420
ttgttcccgt gcgttgcatt tcctgttcac ggcacagcgt gcggaaagca acgttggtta     480
caccagccat gggggctaga accacagggg aggcaaggtc aaaggggccg attttttaaag    540 tcacctaact attgtccccc gtgaatcagg ttgggcaaaa tatttgaagc aaattgtgag     600
cagggcgcaa ctaggaaagt ggtgtgcttt cacttttttgg gggctggggt tgggttaagc    660
ttcgcgggct ctaggggttgg tctgagcttt attcctgggc tttggagggc ttgcaaacag    720
ggggcatgca aatttggggg taatgctggg ccttgaaatc ccactatcac agatagtatt     780
cgggcatttc ctgtcacgat ggtttatcct tgggacacaa catcaaagtg gggtacatca     840
```

```
tatgcttccg gttgaagtga cctatctgaa agattggtc gaaccttgaa gcaatggtgt      900
gaactgcgtt aacgaatttt gtcggacgtt aaaatggtcg cattctgctt gctgaagtgg     960
cacacctatg tgttctgctt gggtatagca gtgcgggaaa aatttgaaaa agtccgatta    1020
cctgaggagg tattca atg tct gat cgc att gct tca gaa aag ctg cgc tcc   1072
              Met Ser Asp Arg Ile Ala Ser Glu Lys Leu Arg Ser
                1               5                  10
```

| | | | | | | | | | | | | | | | | |
|---|---|---|---|---|---|---|---|---|---|---|---|---|---|---|---|---|
| aag ctc atg tcc gcc gac gag gcg gca cag ttt gtt aac cac ggt gac | | | | | | | | | | | | | | | | 1120 |
| Lys Leu Met Ser Ala Asp Glu Ala Ala Gln Phe Val Asn His Gly Asp | | | | | | | | | | | | | | | | |
|       15              20                  25                   | | | | | | | | | | | | | | | | |

```
aag gtt ggt ttc tcc ggc ttc acc ggc gct ggc tac cca aag gca ctg    1168
Lys Val Gly Phe Ser Gly Phe Thr Gly Ala Gly Tyr Pro Lys Ala Leu
         30              35                  40 cct acg gca atc gct aac cgg gct aaa gaa gca cac ggt gca ggc aac    1216
Pro Thr Ala Ile Ala Asn Arg Ala Lys Glu Ala His Gly Ala Gly Asn
 45              50                  55                      60 gac tac gca atc gac ctg ttc act ggc gca tcg acc gcc cct gac tgc    1264
Asp Tyr Ala Ile Asp Leu Phe Thr Gly Ala Ser Thr Ala Pro Asp Cys
                 65                  70                  75 gat ggc gta ctt gca gaa gct gac gct atc cgc tgg cgc atg cca tac    1312
Asp Gly Val Leu Ala Glu Ala Asp Ala Ile Arg Trp Arg Met Pro Tyr
                     80                  85                  90 gca tct gat cca atc atg cgt aac aag atc aac tcc ggc tcc atg gga    1360
Ala Ser Asp Pro Ile Met Arg Asn Lys Ile Asn Ser Gly Ser Met Gly
         95                  100                 105 tac tcc gat atc cac ctg tcc cac tcc ggc cag cag gtt gaa gag ggc    1408
Tyr Ser Asp Ile His Leu Ser His Ser Gly Gln Gln Val Glu Glu Gly
    110                  115                 120 ttc ttc ggc cag ctc aac gta gct gtc att gaa atc acc cgc atc act    1456
Phe Phe Gly Gln Leu Asn Val Ala Val Ile Glu Ile Thr Arg Ile Thr
125                  130                 135                 140 gaa gag ggc tac atc atc cct tct tcc tcc gtg ggt aac aac gtt gag    1504
Glu Glu Gly Tyr Ile Ile Pro Ser Ser Ser Val Gly Asn Asn Val Glu
                 145                 150                 155 tgg ctc aac gct gca gag aag gtc atc ctc gag gtt aac tct tgg cag    1552
Trp Leu Asn Ala Ala Glu Lys Val Ile Leu Glu Val Asn Ser Trp Gln
             160                 165                 170 tct gaa gac ctc gaa ggt atg cac gac atc tgg tct gtt cct gcc ctg    1600
Ser Glu Asp Leu Glu Gly Met His Asp Ile Trp Ser Val Pro Ala Leu
        175                  180                 185 cca aac cgc att gcc gtg cca atc aac aag cca ggc gac cgc atc ggt    1648
Pro Asn Arg Ile Ala Val Pro Ile Asn Lys Pro Gly Asp Arg Ile Gly
    190                  195                 200 aag acc tac atc gag ttc gac acc gac aag gtt gtt gct gtt gtt gag    1696
Lys Thr Tyr Ile Glu Phe Asp Thr Asp Lys Val Val Ala Val Val Glu
205                  210                 215                 220 acc aac acc gca gac cgc aac gca cca ttc aag cct gtc gac gac atc    1744
Thr Asn Thr Ala Asp Arg Asn Ala Pro Phe Lys Pro Val Asp Asp Ile
                 225                 230                 235 tct aag aag atc gct ggc aac ttc ctc gac ttc ctg gaa agc gaa gtt    1792
Ser Lys Lys Ile Ala Gly Asn Phe Leu Asp Phe Leu Glu Ser Glu Val
             240                 245                 250 gct gca ggt cgc ctg tcc tac gac ggc tac atc atg cag tcc ggc gtg    1840
Ala Ala Gly Arg Leu Ser Tyr Asp Gly Tyr Ile Met Gln Ser Gly Val
        255                  260                 265 ggc aac gtg cca aac gcg gtg atg gca ggc ctg ctg gaa tcc aag ttt    1888
Gly Asn Val Pro Asn Ala Val Met Ala Gly Leu Leu Glu Ser Lys Phe
    270                  275                 280 gag aac atc cag gcc tac acc gaa gtt atc cag gac ggc atg gtg gac    1936
Glu Asn Ile Gln Ala Tyr Thr Glu Val Ile Gln Asp Gly Met Val Asp
```

```
                285                 290                 295                 300
ctc atc gac gcc ggc aag atg acc gtt gca tcc gca act tcc ttc tcc    1984
Leu Ile Asp Ala Gly Lys Met Thr Val Ala Ser Ala Thr Ser Phe Ser
                305                 310                 315 ctg tct cct gag tac gca gag aag atg aac aac gag gct aag cgt tac    2032
Leu Ser Pro Glu Tyr Ala Glu Lys Met Asn Asn Glu Ala Lys Arg Tyr
            320                 325                 330 cgc gag tcc att atc ctg cgc cca cag cag atc tct aac cac cca gag    2080
Arg Glu Ser Ile Ile Leu Arg Pro Gln Gln Ile Ser Asn His Pro Glu
                335                 340                 345 gtc atc cgc cgc gtt ggc ctg atc gcc acc aac ggt ctc atc gag gct    2128
Val Ile Arg Arg Val Gly Leu Ile Ala Thr Asn Gly Leu Ile Glu Ala
        350                 355                 360 gac att tac ggc aac gtc aac tcc acc aac gtt tct ggc tcc cgc gtc    2176
Asp Ile Tyr Gly Asn Val Asn Ser Thr Asn Val Ser Gly Ser Arg Val
365                 370                 375                 380 atg aac ggc atc ggc ggc tcc ggc gac ttc acc cgt aac ggc tac atc    2224
Met Asn Gly Ile Gly Gly Ser Gly Asp Phe Thr Arg Asn Gly Tyr Ile
                385                 390                 395 tcc agc ttc atc acc cct tca gag gca aag ggc ggc gca atc tct gcg    2272
Ser Ser Phe Ile Thr Pro Ser Glu Ala Lys Gly Gly Ala Ile Ser Ala
                400                 405                 410 atc gtt cct ttc gca tcc cac atc gac cac acc gag cac gat gtc atg    2320
Ile Val Pro Phe Ala Ser His Ile Asp His Thr Glu His Asp Val Met
            415                 420                 425 gtt gtt atc tct gag tac ggt tac gca gac ctt cgt ggt ctg gct cca    2368
Val Val Ile Ser Glu Tyr Gly Tyr Ala Asp Leu Arg Gly Leu Ala Pro
                430                 435                 440 cgt gag cgc gtt gcc aag atg atc ggc ctg gct cac cct gat tac cgc    2416
Arg Glu Arg Val Ala Lys Met Ile Gly Leu Ala His Pro Asp Tyr Arg
445                 450                 455                 460 cca ctg ctc gag gag tac tac gct cgc gca acc tcc ggt gac aac aag    2464
Pro Leu Leu Glu Glu Tyr Tyr Ala Arg Ala Thr Ser Gly Asp Asn Lys
                465                 470                 475 tac atg cag acc cct cat gat ctt gca acc gcg ttt gat ttc cac atc    2512
Tyr Met Gln Thr Pro His Asp Leu Ala Thr Ala Phe Asp Phe His Ile
            480                 485                 490 aac ctg gct aag aac ggc tcc atg aag gca taa gttttttctt ggtttagaaa  2565
Asn Leu Ala Lys Asn Gly Ser Met Lys Ala
                495                 500 ccgccgcctc gacaacattt cgaggcggcg gtttctttta ttacctgggt tttgagcgtt  2625
aaattagacc aggtcaggct agtgtttggt agctaattga gggcgatttt aataaggccg  2685
gtgccatgta ctaatatggt ctgagttggg cctatagctc agttggtaga gctacggact  2745
tttaatccgc aggtcttggg ttcgagtccc aatgggccca tcttaagt accctgtttt    2805 tggagaatgc tccgagccag gggtactttt cttttcctca cacacagtag ctgctgagaa  2865
aaatgaagac cttttgttag gttgggagta tgaccaaccc atacgaggcc ttcataccgc  2925
tcaagcatcg tacggggatt gaacccgagc acaccttttg gaatgggaa aacaaaaggg   2985 ttcacattgc aaggagacgt cgagaagcgc ccgtccgcgt tatcgtggtg catgggctag  3045
gcacccatag tggcgccctc tggcccctcg tcgcggccat tgagggcgcg acctcgccg   3105 cgatcgacct gcctaaaact ccgctttacg acgattggct gcgcctttta gaatctttca  3165
tctcttccga agacgacggt cggccactca tcctgatcgg tgcaggcacc ggaggcttgc  3225
tttgcgcaga agctgcacac cgcacaggac tggtcgcaca cgtcattgcc acctgcctgc  3285
tcaacccctc cgaccagccg acgcgccggg cactgttcag gttttcaccg ctgactcggt  3345
```

-continued

```
tgatccaagg ccgcttgcgc aaccgcgaaa ttcccgtgac cagagtgttg aacttcagca    3405
aaatcagccg cagcccagcc ctgagcaaat tgtgcgcggc cgatgaattt agcggagcat    3465
ccaaaataac ctggggtttc ctcgcgtcat atgtgcaaca caaggccaaa ctgggtgcag    3525
ttcccgtcac tctgatgcac cctgaccacg accttctgac tcccgttgag ctcagtctgc    3585
gtacgctttc gcgcc                                                     3600
```

<210> SEQ ID NO 24
<211> LENGTH: 502
<212> TYPE: PRT
<213> ORGANISM: Corynebacterium glutamicum

<400> SEQUENCE: 24

```
Met Ser Asp Arg Ile Ala Ser Glu Lys Leu Arg Ser Lys Leu Met Ser
 1               5                  10                  15

Ala Asp Glu Ala Ala Gln Phe Val Asn His Gly Asp Lys Val Gly Phe
            20                  25                  30

Ser Gly Phe Thr Gly Ala Gly Tyr Pro Lys Ala Leu Pro Thr Ala Ile
        35                  40                  45

Ala Asn Arg Ala Lys Glu Ala His Gly Ala Gly Asn Asp Tyr Ala Ile
    50                  55                  60

Asp Leu Phe Thr Gly Ala Ser Thr Ala Pro Asp Cys Asp Gly Val Leu
65                  70                  75                  80

Ala Glu Ala Asp Ala Ile Arg Trp Arg Met Pro Tyr Ala Ser Asp Pro
                85                  90                  95

Ile Met Arg Asn Lys Ile Asn Ser Gly Ser Met Gly Tyr Ser Asp Ile
           100                 105                 110

His Leu Ser His Ser Gly Gln Gln Val Glu Glu Gly Phe Phe Gly Gln
       115                 120                 125

Leu Asn Val Ala Val Ile Glu Ile Thr Arg Ile Thr Glu Glu Gly Tyr
   130                 135                 140

Ile Ile Pro Ser Ser Ser Val Gly Asn Asn Val Glu Trp Leu Asn Ala
145                 150                 155                 160

Ala Glu Lys Val Ile Leu Glu Val Asn Ser Trp Gln Ser Glu Asp Leu
                165                 170                 175

Glu Gly Met His Asp Ile Trp Ser Val Pro Ala Leu Pro Asn Arg Ile
           180                 185                 190

Ala Val Pro Ile Asn Lys Pro Gly Asp Arg Ile Gly Lys Thr Tyr Ile
       195                 200                 205

Glu Phe Asp Thr Asp Lys Val Val Ala Val Glu Thr Asn Thr Ala
   210                 215                 220

Asp Arg Asn Ala Pro Phe Lys Pro Val Asp Asp Ile Ser Lys Lys Ile
225                 230                 235                 240

Ala Gly Asn Phe Leu Asp Phe Leu Glu Ser Glu Val Ala Ala Gly Arg
                245                 250                 255

Leu Ser Tyr Asp Gly Tyr Ile Met Gln Ser Gly Val Gly Asn Val Pro
            260                 265                 270

Asn Ala Val Met Ala Gly Leu Leu Glu Ser Lys Phe Glu Asn Ile Gln
        275                 280                 285

Ala Tyr Thr Glu Val Ile Gln Asp Gly Met Val Asp Leu Ile Asp Ala
    290                 295                 300

Gly Lys Met Thr Val Ala Ser Ala Thr Ser Phe Ser Leu Ser Pro Glu
305                 310                 315                 320

Tyr Ala Glu Lys Met Asn Asn Glu Ala Lys Arg Tyr Arg Glu Ser Ile
                325                 330                 335
```

```
Ile Leu Arg Pro Gln Gln Ile Ser Asn His Pro Glu Val Ile Arg Arg
                340                 345                 350

Val Gly Leu Ile Ala Thr Asn Gly Leu Ile Glu Ala Asp Ile Tyr Gly
            355                 360                 365

Asn Val Asn Ser Thr Asn Val Ser Gly Ser Arg Val Met Asn Gly Ile
        370                 375                 380

Gly Gly Ser Gly Asp Phe Thr Arg Asn Gly Tyr Ile Ser Ser Phe Ile
385                 390                 395                 400

Thr Pro Ser Glu Ala Lys Gly Gly Ala Ile Ser Ala Ile Val Pro Phe
                405                 410                 415

Ala Ser His Ile Asp His Thr Glu His Asp Val Met Val Val Ile Ser
            420                 425                 430

Glu Tyr Gly Tyr Ala Asp Leu Arg Gly Leu Ala Pro Arg Glu Arg Val
        435                 440                 445

Ala Lys Met Ile Gly Leu Ala His Pro Asp Tyr Arg Pro Leu Leu Glu
    450                 455                 460

Glu Tyr Tyr Ala Arg Ala Thr Ser Gly Asp Asn Lys Tyr Met Gln Thr
465                 470                 475                 480

Pro His Asp Leu Ala Thr Ala Phe Asp Phe His Ile Asn Leu Ala Lys
                485                 490                 495

Asn Gly Ser Met Lys Ala
            500
```

<210> SEQ ID NO 25
<211> LENGTH: 2037
<212> TYPE: DNA
<213> ORGANISM: Corynebacterium glutamicum
<220> FEATURE:
<221> NAME/KEY: CDS
<222> LOCATION: (573)..(1913)

<400> SEQUENCE: 25

```
gctagcctcg ggagctctag gagattgtga aaaacgggtc aaatttctcc gatgcagcgc      60
ctataaaagt cgtaccaatt ccatttgagg gtgctcaagt gtggccaggt tatataacca     120
gtcagtcaac tggtctcatt cgctggtcgg atgaatttaa ttaaagaaga gacttcatgc     180
agttaccgcg cgttttggcg atacacaatt gataaaccta agaaattttt caaacaattt     240
taattctttg tggtcatatc tgtgcgacac tgccataatt gaacgtgagc atttaccagc     300
ctaaatgccc gcagtgagtt aagtctcaaa gcaagaagtt gctctttagg gcatccgtag     360
tttaaaacta ttaaccgtta ggtatgacaa gccggttgat gtgaacgcag ttttttaaaag    420 tttcaggatc agattttttca caggcatttt gctccagcaa acgcctagga tgtacatggt    480
gccctcaatg ggaaccacca acatcactaa atggcccaga tacacacttt aaaatcgtgc     540
gcgcatgcag ccgagatggg aacgaggaaa tc atg aca gtt gat gag cag gtc       593
                                    Met Thr Val Asp Glu Gln Val
                                      1               5 tct aac tat tac gac atg ctt ctg aag cgc aat gct ggc gag cct gaa       641
Ser Asn Tyr Tyr Asp Met Leu Leu Lys Arg Asn Ala Gly Glu Pro Glu
        10                  15                  20 ttt cac cag gca gtg gca gag gtt ttg gaa tct ttg aag atc gtc ctg       689
Phe His Gln Ala Val Ala Glu Val Leu Glu Ser Leu Lys Ile Val Leu
    25                  30                  35 gaa aag gac cct cat tac gct gat tac ggt ctc atc cag cgc ctg tgc       737
Glu Lys Asp Pro His Tyr Ala Asp Tyr Gly Leu Ile Gln Arg Leu Cys
40                  45                  50                  55 gag cct gag cgt cag ctc atc ttc cgt gtg cct tgg gtt gat gac cag       785
```

-continued

```
Glu Pro Glu Arg Gln Leu Ile Phe Arg Val Pro Trp Val Asp Asp Gln
              60                  65                  70 ggc cag gtc cac gtc aac cgt ggt ttc cgc gtg cag ttc aac tct gca       833
Gly Gln Val His Val Asn Arg Gly Phe Arg Val Gln Phe Asn Ser Ala
         75                  80                  85 ctt gga cca tac aag ggc ggc ctg cgc ttc cac cca tct gta aac ctg       881
Leu Gly Pro Tyr Lys Gly Gly Leu Arg Phe His Pro Ser Val Asn Leu
         90                  95                 100 ggc att gtg aag ttc ctg ggc ttt gag cag atc ttt aaa aac tcc cta       929
Gly Ile Val Lys Phe Leu Gly Phe Glu Gln Ile Phe Lys Asn Ser Leu
        105                 110                 115 acc ggc ctg cca atc ggt ggt ggc aag ggt gga tcc gac ttc gac cct       977
Thr Gly Leu Pro Ile Gly Gly Gly Lys Gly Gly Ser Asp Phe Asp Pro
120             125                 130                 135 aag ggc aag tcc gat ctg gaa atc atg cgt ttc tgc cag tcc ttc atg      1025
Lys Gly Lys Ser Asp Leu Glu Ile Met Arg Phe Cys Gln Ser Phe Met
            140                 145                 150 acc gag ctg cac cgc cac atc ggt gag tac cgc gac gtt cct gca ggt      1073
Thr Glu Leu His Arg His Ile Gly Glu Tyr Arg Asp Val Pro Ala Gly
            155                 160                 165 gac atc gga gtt ggt ggc cgc gag atc ggt tac ctg ttt ggc cac tac      1121
Asp Ile Gly Val Gly Gly Arg Glu Ile Gly Tyr Leu Phe Gly His Tyr
        170                 175                 180 cgt cgc atg gcc aac cag cac gag tcc ggc gtt ttg acc ggt aag ggc      1169
Arg Arg Met Ala Asn Gln His Glu Ser Gly Val Leu Thr Gly Lys Gly
        185                 190                 195 ctg acc tgg ggt gga tcc ctg gtc cgc acc gag gca act ggc tac ggc      1217
Leu Thr Trp Gly Gly Ser Leu Val Arg Thr Glu Ala Thr Gly Tyr Gly
200             205                 210                 215 tgc gtt tac ttc gtg agt gaa atg atc aag gct aag ggc gag agc atc      1265
Cys Val Tyr Phe Val Ser Glu Met Ile Lys Ala Lys Gly Glu Ser Ile
                220                 225                 230 agc ggc cag aag atc atc gtt tcc ggt tcc ggc aac gta gca acc tac      1313
Ser Gly Gln Lys Ile Ile Val Ser Gly Ser Gly Asn Val Ala Thr Tyr
            235                 240                 245 gcg att gaa aag gct cag gaa ctc ggc gca acc gtt att ggt ttc tcc      1361
Ala Ile Glu Lys Ala Gln Glu Leu Gly Ala Thr Val Ile Gly Phe Ser
            250                 255                 260 gat tcc agc ggt tgg gtt cat acc cct aat ggc gtt gac gtg gct aag      1409
Asp Ser Ser Gly Trp Val His Thr Pro Asn Gly Val Asp Val Ala Lys
265                 270                 275 ctc cgc gaa atc aag gaa gtt cgc cgc gca cgc gta tcc gtg tac gcc      1457
Leu Arg Glu Ile Lys Glu Val Arg Arg Ala Arg Val Ser Val Tyr Ala
280                 285                 290                 295 gac gaa gtt gaa ggc gca acc tac cac acc gac ggg tcc atc tgg gat      1505
Asp Glu Val Glu Gly Ala Thr Tyr His Thr Asp Gly Ser Ile Trp Asp
                300                 305                 310 ctc aag tgc gat atc gct ctt cct tgt gca act cag aac gag ctc aac      1553
Leu Lys Cys Asp Ile Ala Leu Pro Cys Ala Thr Gln Asn Glu Leu Asn
            315                 320                 325 ggt gag aac gct aag act ctt gca gac aac ggc tgc cgt ttc gtt gct      1601
Gly Glu Asn Ala Lys Thr Leu Ala Asp Asn Gly Cys Arg Phe Val Ala
            330                 335                 340 gaa ggc gcg aac atg cct tcc acc cca gag gct gtt gag gtc ttc cgt      1649
Glu Gly Ala Asn Met Pro Ser Thr Pro Glu Ala Val Glu Val Phe Arg
345                 350                 355 gag cgc gac atc cgc ttc gga cca ggc aag gca gct aac gct ggt ggc      1697
Glu Arg Asp Ile Arg Phe Gly Pro Gly Lys Ala Ala Asn Ala Gly Gly
360                 365                 370                 375 gtt gca acc tcc gct ctg gag atg cag cag aac gct tcg cgc gat tcc      1745
```

-continued

```
                Val Ala Thr Ser Ala Leu Glu Met Gln Gln Asn Ala Ser Arg Asp Ser
                                380                 385                 390 tgg agc ttc gag tac acc gac gag cgc ctc cag gtg atc atg aag aac     1793
Trp Ser Phe Glu Tyr Thr Asp Glu Arg Leu Gln Val Ile Met Lys Asn
            395                 400                 405 atc ttc aag acc tgt gca gag acc gca gca gag tat gga cac gag aac     1841
Ile Phe Lys Thr Cys Ala Glu Thr Ala Ala Glu Tyr Gly His Glu Asn
        410                 415                 420 gat tac gtt gtc ggc gct aac att gct ggc ttc aag aag gta gct gac     1889
Asp Tyr Val Val Gly Ala Asn Ile Ala Gly Phe Lys Lys Val Ala Asp
    425                 430                 435 gcg atg ctg gca cag ggc gtc atc taa gaccctgca ctttacttaa            1936
Ala Met Leu Ala Gln Gly Val Ile
440                 445 acccctgatc cgcgttaagg atcagggatt tttgatttct tccaggtcaa ttatccgatc   1996
cacatgggtt aatgcagctg tgcggtgcgc aatgatgatc a                       2037

<210> SEQ ID NO 26
<211> LENGTH: 447
<212> TYPE: PRT
<213> ORGANISM: Corynebacterium glutamicum

<400> SEQUENCE: 26

Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140

Arg Phe Cys Gln Ser Phe Met Thr Glu Leu His Arg His Ile Gly Glu
145                 150                 155                 160

Tyr Arg Asp Val Pro Ala Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
    210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
```

-continued

```
                        260                 265                 270
Asn Gly Val Asp Val Ala Lys Leu Arg Glu Ile Lys Glu Val Arg Arg
            275                 280                 285
Ala Arg Val Ser Val Tyr Ala Asp Glu Val Glu Gly Ala Thr Tyr His
            290                 295                 300
Thr Asp Gly Ser Ile Trp Asp Leu Lys Cys Asp Ile Ala Leu Pro Cys
305                 310                 315                 320
Ala Thr Gln Asn Glu Leu Asn Gly Glu Asn Ala Lys Thr Leu Ala Asp
            325                 330                 335
Asn Gly Cys Arg Phe Val Ala Glu Gly Ala Asn Met Pro Ser Thr Pro
            340                 345                 350
Glu Ala Val Glu Val Phe Arg Glu Arg Asp Ile Arg Phe Gly Pro Gly
            355                 360                 365
Lys Ala Ala Asn Ala Gly Gly Val Ala Thr Ser Ala Leu Glu Met Gln
            370                 375                 380
Gln Asn Ala Ser Arg Asp Ser Trp Ser Phe Glu Tyr Thr Asp Glu Arg
385                 390                 395                 400
Leu Gln Val Ile Met Lys Asn Ile Phe Lys Thr Cys Ala Glu Thr Ala
                405                 410                 415
Ala Glu Tyr Gly His Glu Asn Asp Tyr Val Val Gly Ala Asn Ile Ala
                420                 425                 430
Gly Phe Lys Lys Val Ala Asp Ala Met Leu Ala Gln Gly Val Ile
            435                 440                 445
```

L-AMINO ACID-PRODUCING BACTERIUM AND A METHOD FOR PRODUCING L-AMINO ACID

The present invention claims priority under 35 U.S.C. §119 to Japanese Patent Application No. 2004-340187, filed Nov. 25, 2004, and is a continuation under 35 U.S.C. §120 of PCT/JP2005/022137, filed Nov. 25, 2005, the entirety of both of which is incorporated by reference. Also, the Sequence Listing filed electronically herewith is hereby incorporated by reference (File name: US-255_Seq_List_Copy_1; File size: 49 KB; Date recorded: May 25, 2007).

BACKGROUND OF THE INVENTION

1. Field of the Invention

The present invention relates to a method for producing L-amino acids generated via a biosynthetic pathway in which pyruvic acid is an intermediate during fermentation of coryneform bacteria. The L-amino acids which can be generated via this method are L-glutamic acid, L-arginine, L-glutamine, L-proline, L-valine, L-alanine, and L-lysine.

2. Brief Description of the Related Art

An L-amino acid such as L-glutamic acid is generated via a biosynthetic pathway in which pyruvic acid is an intermediate. L-amino acids are conventionally produced on an industrial scale by fermentative methods utilizing coryneform bacteria, including *Brevibacterium* and *Corynebacterium*. To improve the L-amino acid-productivity of coryneform bacteria, strains isolated from nature or artificial mutants thereof have been used. (JP07-121228B, JP07-121228B, JP06-237779A, Adv Biochem Eng Biotechnol. 2003; 79:59-112. J. Biotechnol. 2003 Sep. 4; 104(1-3):155-72. and WO95/34672)

When aerobic bacteria, especially coryneform bacteria, are cultured under oxygen-limited conditions, organic acids other than the target substance, such as lacetic acid and acetic acid, accumulate in excess amounts as byproducts. Such accumulation inhibits the growth of the bacteria and greatly reduces their productivity during fermentation. Furthermore, excess amounts of counter ions which neutralize such organic acids are necessary, which increases the production cost. Accordingly, creating strains that produce less acetic acid during culture is desirable, such as strains in which the activity of an enzyme that catalyzes production of acetic acid is reduced or eliminated.

Examples of fermentation methods using a strain in which the activity of an enzyme that catalyzes production of acetic acid is reduced or eliminated include producing L-amino acids using *Escherichia coli* which is deficient in the activities of phosphoacetyltransferase (pta) and lactate dehydrogenase (ldh) (WO99/06532), producing L-amino acids using Enterobacteriaceae family which is deficient in the activity of pyruvate oxidase (poxB), and producing D-panthotheic acid using Enterobacteriaceae which is deficient in the activity of pyruvate oxidase (poxB) (WO02/36797).

Acetate kinase (ack) and phosphotransacetylase (pta) have been reported as enzymes that are involved in the assimilation of acetic acid in coryneform bacteria (Microbiology, 1999 February; 145(Pt2):503-13). Also, a coryneform bacterium in which the acetate-producing enzyme pyruvate oxidase (poxB) is disrupted has been reported (EP1096013A).

Acetyl-CoA hydrolase (3.1.2.1) produces acetic acid from acetyl-CoA and $H_2O$, and the nucleotide sequence predicted to encode acetyl-coA hydrolase of *Corynebacterium glutamicum* has been disclosed (EP1108790A). However, there has been no report on the actual cloning and expression analysis of the gene; and thus the actual function of the gene has not been confirmed yet.

SUMMARY OF THE INVENTION

An object of the present invention is to provide a coryneform bacterium which has an improved ability to produce L-amino acids which are generated by a biosynthetic pathway in which pyruvic acid is an intermediate, and to provide a method of efficiently producing the above-mentioned L-amino acids using such a bacterium. As described herein, it has been found that by decreasing acetyl-CoA hydrolase activity in a coryneform bacterium, the ability to produce L-amino acids, particularly L-glutamic acid, L-valine, and L-alanine is increased.

It is an object of the present invention to provide a coryneform bacterium having an L-amino acid-producing ability, wherein said coryneform bacterium is modified so that acetyl-CoA hydrolase activity is decreased, and wherein said L-amino acid is one or more L-amino acids generated by biosynthetic pathway in which pyruvic acid is an intermediate.

It is a further object of the present invention to provide the coryneform bacterium as described above, wherein said acetyl-CoA hydrolase activity is decreased by introducing a mutation into the coding region or the expression regulatory region of the chromosomal acetyl-CoA hydrolase gene.

It is a further object of the present invention to provide the coryneform bacterium as described above, wherein said acetyl-CoA hydrolase activity is decreased by disrupting the chromosomal acetyl-CoA hydrolase gene.

It is a further object of the present invention to provide the coryneform bacterium as described above, wherein said acetyl-CoA hydrolase is selected from the group consisting of:

(A) a protein comprising the amino acid sequence shown in SEQ ID NO: 24; and (B) a protein comprising the amino acid sequence shown in SEQ ID NO: 24, whereby one or several amino acids in said protein are substituted, deleted, inserted, or added, and wherein said protein has acetyl-CoA hydrolase activity.

It is a further object of the present invention to provide the coryneform bacterium as described above, wherein said acetyl-CoA hydrolase gene is selected from the group consisting of:

(a) a gene comprising nucleotides 1037 to 2542 of SEQ ID NO: 23; and (b) a DNA that is able to hybridize under stringent conditions to a polynucleotide comprising nucleotides 1037 to 2542 of SEQ ID NO: 23 or a probe prepared from said polynucleotide, and wherein said DNA encodes a protein having acetyl-CoA hydrolase activity.

It is a further object of the present invention to provide the coryneform bacterium as described above, wherein said coryneform bacterium is further modified to increase glutamic acid dehydrogenase activity.

It is a further object of the present invention to provide the coryneform bacterium as described above, wherein said L-amino acid is selected from the group consisting of L-glutamic acid, L-arginine, L-glutamine, L-proline, L-alanine, L-valine L-lysine, and combinations thereof.

It is a further object of the present invention to provide a method for producing an L-amino acid comprising:

culturing the coryneform bacterium as described above in a medium; and collecting the L-amino acid from the medium, and wherein said L-amino acid is one or more L-amino acids generated by a biosynthetic pathway in which pyruvic acid is an intermediate.

It is a further object of the present invention to provide the method as described above, wherein said L-amino acids are selected from the group consisting of L-glutamic acid, L-arginine, L-glutamine, L-proline, L-alanine, L-valine, and L-lysine, and combinations thereof.

DESCRIPTION OF THE PREFERRED EMBODIMENTS

Figure 1:
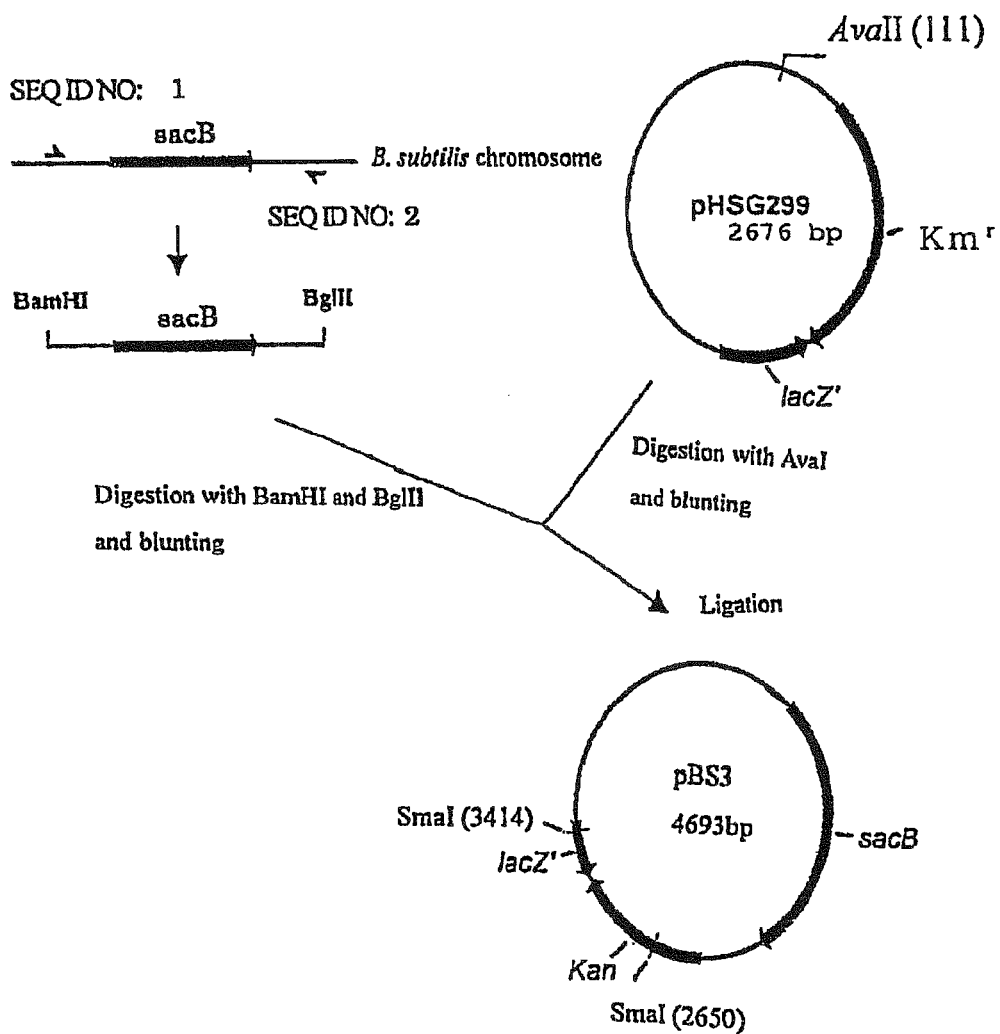
FIG. 1 is a scheme showing the procedure for constructing plasmid pBS3.

Hereinafter, embodiments of the present invention will be described in detail.

<1> Coryneform bacterium having Ability to Produce L-Amino Acids Generated by a Biosynthetic Pathway in which Pyruvic Acid is an Intermediate In the present invention, examples of coryneform bacterium include conventional coryneform bacterium, and also include bacteria that had been classified into the genus *Brevibacterium*, but are currently classified into the genus *Corynebacterium* (Int. J. Syst. Bacteriol., 41, 255(1991)), as well as the *Brevibacterium* bacteria that are very close to *Corynebacterium* bacteria. Examples of such *coryneform bacterium* include the following:

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Brevibacterium ammoniagenes*
*Brevibacterium album*
*Brevibacterium cerinum*
*Microbacterium ammoniaphilum*

Specific examples of the coryneform bacterium are as follows.

*Corynebacterium acetoacidophilum* ATCC13870
*Corynebacterium acetoglutamicum* ATCC15806
*Corynebacterium alkanolyticum* ATCC21511
*Corynebacterium callunae* ATCC15991
*Corynebacterium glutamicum* ATCC13020, ATCC13032, ATCC13060, ATCC13869
*Corynebacterium lilium* ATCC15990
*Corynebacterium melassecola* ATCC17965
*Corynebacterium thermoaminogenes* AJ12340 (FERM BP-1539)
*Corynebacterium herculis* ATCC13868
*Brevibacterium divaricatum* ATCC14020
*Brevibacterium flavum* ATCC13826, ATCC14067, AJ12418 (FERM BP-2205)
*Brevibacterium immariophilum* ATCC14068
*Brevibacterium lactofermentum* (*Corynebacterium glutamicum*) ATCC13869
*Brevibacterium roseum* ATCC13825
*Brevibacterium saccharolyticum* ATCC14066
*Brevibacterium thiogenitalis* ATCC19240
*Brevibacterium ammoniagenes* ATCC6871, ATCC6872
*Brevibacterium album* ATCC15111
*Brevibacterium cerinum* ATCC15112
*Microbacterium ammoniaphilum* ATCC15354

These strains are available from the American Type Culture Collection (ATCC, Address: P.O. Box 1549, Manassas, Va. 20108, United States of America). That is, each strain is given a unique registration number which is listed in the catalogue of the ATCC. Strains can be ordered using this registration number. The AJ12340 strain was deposited at the National Institute of Bioscience and Human Technology, Agency of Industrial Science and Technology, Ministry of International Trade and Industry (currently International Patent Organism Depositary, National Institute of Advanced Industrial Science and Technology at Tsukuba Central 6, 1-1, Higashi 1-chome, Tsukuba-shi, Ibaraki-ken 305-5466, Japan) on Oct. 27, 1989 under the provisions of the Budapest Treaty and given an accession number of FERM BP-1539. The AJ12418 strain was deposited at the National Institute of Bioscience and Human Technology, Agency of Industrial Science and Technology, Ministry of International Trade and Industry on Jan. 5, 1989 under the provisions of the Budapest Treaty and given an accession number of FERM BP-2205.

"L-amino acids generated by a biosynthetic pathway in which pyruvic acid is an intermediate" preferably means those L-amino acids which have carbon skeletons derived from pyruvic acid. Examples of such L-amino acids include L-glutamic acid, L-arginine, L-glutamine, L-proline, L-alanine, L-valine, and L-lysine. As used herein, "the ability to produce L-amino acids by a biosynthetic pathway in which pyruvic acid is an intermediate" refers to the ability of the coryneform bacteria to generate or produce one or more of the above-mentioned L-amino acids in a medium when the bacteria are cultured in the medium.

The ability to produce L-amino acids may be a native ability of a wild-type strain of coryneform bacterium, or an ability which has been imparted by breeding. Furthermore, the ability to produce L-amino acids may be imparted by a modification which results in the decrease in acetyl-CoA hydrolase activity, as described later.

To impart L-amino acid-producing ability, conventional methods typically used in breeding coryneform bacteria can be used, such as the creation of metabolic-regulation mutant strains, or the creation of recombinant strains which have enhanced activity of biosynthetic enzymes of target substances ("Amino Acid Fermentation", Center for Academic Publications Japan Co., Ltd., 1st ed. published on May 30, 1986, p. 77 to 100). In these methods, introducing a metabolic-regulation mutation, and enhancing target-substance-biosynthetic enzymes may be used singly, or in combination.

Furthermore, two or more mutations may be introduced, and two or more enzymatic activities may be enhanced.

An example of a method for imparting L-glutamic acid-producing ability is to enhance the expression of a gene encoding an L-glutamic acid biosynthetic enzyme. Examples of the enzymes involved in L-glutamic acid biosynthesis include glutamate dehydrogenase, glutamine synthetase, glutamate synthetase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde-3-phophate dehydrogenase, triose phosphate isomerase, fructose bisphosphate aldolase, phosphofructokinase, and glucose phosphate isomerase.

Enhancing expression of these genes may be achieved by inserting a DNA fragment containing such a gene into an appropriate plasmid which is autonomously replicable in coryneform bacterium, and transforming bacterial cells with the resulting plasmid; by integrating such a gene into a chromosome by homologous recombination, conjugation, transposition (EP0756007B, EP0332488A EP0771879A), etc.; or by introducing a mutation into a promoter region of such a gene (WO/0018935) or substituting the native promoter with a strong promoter.

When the above-mentioned genes are introduced by a plasmid or integrated into a chromosome, a promoter for expression of the genes may be any promoter so long as it is able to function in coryneform bacteria. Examples of such promoters include the lac promoter, trp promoter, trc promoter, PS2 promoter, and pL promoter. A native promoter for each gene may also be used.

Examples of microorganisms modified so that expression of the citrate synthetase gene, the phosphoenolpyruvate carboxylase gene, and/or the glutamate dehydrogenase gene is/are enhanced include those microorganisms disclosed in JP2001-333769A (EP1078989A), JP2000-106869A (EP955368A), JP2000-189169A (EP952221A), and JP2001-333769A (EP1078989A).

The modification for imparting the L-glutamic acid-producing ability also includes decreasing or eliminating an activity of an enzyme that catalyzes synthesis of a compound other than L-glutamic acid, and branching off from an L-glutamic acid biosynthesis pathway. Examples of such enzymes include isocitrate lyase, α-ketoglutarate dehydrogenase, phosphotransacetylase, acetate kinase, acetohydroxy acid synthase, acetolactate synthase, formate acetyltransferase, lactate dehydrogenase, and glutamate decarboxylase.

To decrease or eliminate the activity of the above-described enzymes, a mutation or deletion which causes a decrease or loss of the activity of the enzymes may be introduced into the genes of the enzymes on the chromosome. This may be achieved, for example, by disrupting a gene encoding the enzyme on the chromosome, or by modifying an expression control sequence such as a promoter and/or Shine Dargarno (SD) sequence of the gene. In addition, activities of such enzymes may be decreased or eliminated by introducing a missense mutation which causes an amino acid substitution, a nonsense mutation which generates a stop codon, or a frameshift mutation which adds or deletes one or two nucleotides into the coding region, or by deleting a portion of the gene (Journal of biological Chemistry 272:8611-8617 (1997)). Furthermore, the activities of such enzymes may be decreased or eliminated by constructing a gene encoding a mutant enzyme having its coding region deleted and replacing a chromosomal gene with the resulting gene by homologous recombination. Examples of coryneform bacterium in which the α-ketoglutarate dehydrogenase activity is decreased include strains disclosed in JP7-834672A and JP06-237779.

Furthermore, an example of a method of imparting L-glutamic acid-producing ability includes a method of modifying a strain to enhance expression of a gene encoding the yggB gene or to introduce a mutation into the yggB gene. (NCgl 1221□NP_600492. Reports small-conductance . . . [gi: 19552490]□(U.S. Patent application No. 60/715,131)

The L-glutamic acid-producing ability may also be imparted by screening a strain resistant to organic acid analogues, respiratory inhibitors, or superoxide generators, or by screening a strain sensitive to inhibitors of cell wall synthesis. Examples of such methods include imparting resistance to benzopirone or naphtoquinone (JP56-1889A), imparting resistance to monofluoroacetic acid (JP:50-113209A), imparting resistance to adenine and thymine□JP57-065198□imparting resistance to HOQNO (JP56-140895A), imparting resistance to α-ketomalonic acid (JP57-2689A), imparting resistance to guanidine (JP56-35981A), imparting resistance to daunomicin (JP58-158192A), and imparting sensitivity to penicillin (JP04-88994A).

Specific examples of such bacteria include the following strains.

Brevibacterium flavum AJ3949 (FERM BP-2632□JP 50-113209A)

Corynebacterium glutamicum AJ11628 (FERM P-5736□JP 57-065198A)

Brevibacterium flavum AJ11355 (FERM P-5007; JP56-1889A)

Corynebacterium glutamicum AJ11355 (FERM P-5020; JP56-1889A)

Brevibacterium flavum AJ11217 (FERM P-4318; JP57-2689A)

Corynebacterium glutamicum AJ11218 (FERM P-4319; JP57-2689A)

Brevibacterium flavum AJ11564 (FERM P-5472; JP56-140895A)

Brevibacterium flavum AJ11439 (FERM P-5136; JP56-35981A)

Corynebacterium glutamicum H7684 (FERM BP-3004; JP04-88994A)

Brevibacterium lactofermentum AJ11426□FERM P5123 JP56-048890A□

Corynebacterium glutamicum AJ11440□FERM P5137 JP56-048890A□

Brevibacterium lactofermentum AJ11796 (FERM P6402 JP58-158192A)

An example of a method of imparting L-valine-producing ability includes a method of modifying a strain to enhance expression of a gene encoding an L-valine biosynthetic enzyme. Examples of an L-valine-biosynthetic enzyme include enzymes encoded by genes present on the ilvBNC operon, that is, acetohydroxy acid synthetase encoded by ilvBN and isomero-reductase encoded by ilvC (WO00/50624). The ilvBNC operon is subject to transcriptional repression by any combination of L-valine, L-isoleucine, and L-leucine, so that it is desirable to release attenuation to avoid transcriptional repression by L-valine as a product.

Imparting L-valine-producing ability to coryneform bacteria may be performed by decreasing or eliminating the activity of at least one enzyme which catalyzes a reaction that decreases production of L-valine. For example, L-valine-producing ability may be imparted by decreasing the activity of threonine dehydratase, which catalyzes L-leucine synthesis, or by decreasing the activity of an enzyme that catalyzes D-panthothenate synthesis (WO00/50624).

L-valine-producing ability may also be imparted by imparting resistance to amino acid analogs or the like to a coryneform bacterium.

For example, L-valine-producing mutant strains which are auxotrophic for L-isoleucine and L-methionine, and resistant to D-ribose, purine ribonucleo side or pyrimidine ribonucleoside (FERM P-1841, FERM P-29, JP-B-53-025034), L-valine-producing mutant strains resistant to polyketides (FERM P-1763, FERM P-1764; JP-B006-065314), L-valine-producing mutant strains resistant to L-valine and sensitive to pyruvic acid analogs such as β-fluoropyruvic acid (FERM BP-3006, BP-3007, Patent 3006929) may be used.

Examples of coryneform bacteria having L-alanine-producing ability include coryneform bacteria deficient in H⁺-ATPase activity (Appl Microbiol Biotechnol. 2001 November; 57(4):534-40), and coryneform bacteria with an amplified structural gene encoding aspartic acid β-decarboxylase (JP-A-7-163383).

L-arginine-producing ability may be imparted by modifying coryneform bacteria to enhance expression of a gene encoding an L-arginine biosynthetic enzyme. Examples of an L-arginine biosynthetic enzyme include N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase. These arginine biosynthetic genes exist on the Arg operon (argCJBDFRGH), and are regulated by the arginine repressor encoded by argR. (J. Bacteriol. 2002 December; 184(23): 6602-14.) Therefore, the disruption of the arginine repressor results in an increase in the expression of the Arg operon, and thus enhances the activities of the L-arginine-producing enzymes (US2002-0045223).

Another method for imparting L-arginine-producing ability is, for example, by imparting resistance to amino acid analogs. Examples of coryneform bacterium include coryneform bacteria resistant to 2-thiazolealanine, and auxotrophic for L-histidine, L-proline, L-threonine, L-isoleucine, L-methionine, or L-tryptophan (JP-A-54-044096); coryneform bacteria resistant to ketomalonic acid, fluoromalonic acid or monofluoroacetic acid (JP-A-57-18989); coryneform bacterium resistant to argininol (JP-B-62-024075); and coryneform bacterium resistant to x-guanidine (x is a fatty acid or an aliphatic chain derivative) (JP-A-2-186995); and coryneform bacterium resistant to arginine hydroxamate and 6-azauracil (JP-A-57-150381).

An example of a method for imparting L-glutamine-producing ability is by modifying a coryneform bacterium to enhance expression of a gene that encodes an L-glutamine biosynthetic enzyme. Examples of L-glutamine biosynthetic enzymes include glutamine synthetase and glutamic acid dehydrogenase (US2003-0003550).

L-glutamine-producing ability may also be imparted by decreasing or eliminating the activity of an enzyme that catalyzes a reaction branching off from the L-glutamine biosynthetic pathway and producing other compounds. For example, L-glutamine-producing ability may be imparted by decreasing glutaminase activity (US2004-0152175).

L-glutamine-producing ability may also be imparted by imparting L-amino acid analog-resistance. Examples of such methods include imparting resistance to 6-diazo-5-oxo-norleucine (JP-A-3-232497), imparting resistance to purine analogs and/or methionine sulfoxide (JP-A-61-202694), imparting resistance to α-ketomalonic acid (JP-A-56-151495), and imparting resistance to glutamic acid-containing peptide (JP-2-186994).

Specific examples of L-glutamine-producing coryneform bacteria include the following strains.

*Brevibacterium flavum* AJ11573 (FERM P-5492, JP56-161495A)

*Brevibacterium flavum* AJ11576 (FERM BP-10381, JP56-161495A)

*Brevibacterium flavum* AJ12212 (FERM P-8123, JP61-202694A)

*Brevibacterium flavum* AJ12418 (FERM BP-2205, JP02-186994A)

*Brevibacterium flavum* DH18 (FERM P-11116, JP03-232497A)

*Corynebacterium melassecola* DH344 (FERM P-11117, JP3-232497A)

*Corynebacterium glutamicum* AJ11574 (FERM P-5493, JP56-151495A)

An example of a method of imparting L-proline-producing ability includes a method of modifying a coryneform bacterium to enhance expression of a gene encoding an L-proline-biosynthetic enzyme. Examples of L-proline-biosynthetic enzymes include glutamate kinase, γ-glutamyl phosphate reductase, and pyrroline-5-carboxylate reductase. □J. Bacteriol. 1996 August; 178(15):4412-9.□

L-proline-producing ability may also be imparted by decreasing or eliminating the activity of an enzyme that catalyzes a reaction branching off from the L-proline biosynthetic pathway and producing other compounds. For example, L-proline-producing ability may be imparted by decreasing ornithine-aminotransferase activity. □J. Bacteriol. 1996 August; 178(15):4412-9.□

Meanwhile, L-arginine, L-glutamine, and L-proline contain L-glutamic acid as a carbon skeleton, so the ability to produce these amino acids may be imparted by amplifying a gene that encodes an enzyme catalyzing a reaction which results in producing each L-amino acid from L-glutamic acid in the above-mentioned L-glutamic acid-producing bacterium.

Furthermore, since L-alanine is synthesized by β-decarboxylation of L-aspartic acid, L-alanine-producing bacterium may be obtained by modifying the L-aspartic acid-producing bacterium so that acetyl-CoA hydrolase activity is decreased.

Breeding to impart or enhance L-lysine productivity can be performed by introducing one or more mutations as follows. Such artificial mutants are as follows: S-(2-aminoethyl)cysteine (hereinafter referred to as "AEC") resistant mutants; mutants requiring amino acids such as L-homoserine for their growth (see Japanese Patent Publication Nos. 4828078 and 566499); mutants resistant to AEC and requiring amino acids such as L-leucine, L-homoserine, L-proline, L-serine, L-arginine, L-alanine, L-valine, etc. (see U.S. Pat. Nos. 3,708,395 and 3,825,472); L-lysine-producing mutants resistant to DL-amino caprolactam, aminolauryllactam, aspartic acid analogues, sulfa drugs, quinoids and N-lauroylleucine, and L-lysine-producing mutants resistant to oxaloacetate decarboxylase or respiratory system enzyme inhibitors (see Japanese Patent Laid-Open Nos. 5053588, 5031093, 52102498, 539394, 5386089, 559783, 559759, 5632995, 5639778, Japanese Patent Publication Nos. 5343591, 531833); L-lysine-producing mutants requiring inositol or acetic acid (see Japanese Patent Laid-Open Nos. 559784, 568692); L-lysine-producing mutants sensitive to fluoropyruvic acid or to temperatures of 34 C or higher (see Japanese Patent Laid Open No. 5386090); L-lysine-producing mutants of *Brevibacterium* or *Corynebacterium* resistant to ethylene glycol (see U.S. Pat. No. 4,411,997).

An example of a method for imparting L-lysine-producing ability is to enhance the expression of a gene encoding an L-lysine biosynthetic enzyme. Examples of the enzymes involved in L-lysine biosynthesis include, but are not limited to, diaminopimelate pathway enzymes, such as the dihydrodipicolinate synthase gene (dapA), the aspartokinase gene (lysC), the dihydrodipicolinated reductase gene (dapB), the diaminopimelate decarboxylase gene (lysA), the diaminopimelate dehydrogenase gene (ddh) (all of the foregoing; International Publication No. 96/40934), the phosphoenolpyrvate carboxylase gene (ppc) (Japanese Patent Application Laid-Open No. 60-87788), the aspartate aminotransferase gene (aspC) (Japanese Patent Publication No. 6-102028), the diaminopimelate epimerase gene (dapF) (Japanese Patent Application Laid-Open No. 2003-135066), and the aspartate semialdehyde dehydrogenease gene (asd) (International Publication No. 00/61723), and the aminoadipate pathway enzymes, such as the homoaconitate hydratase gene (Japanese Patent Application Laid-Open No. 2000-157276).

Furthermore, the bacterium of the present invention may have decreased activity of an enzyme that catalyzes a reaction for generating a compound other than L-lysine by branching off from the biosynthetic pathway of L-lysine, or may be deficient in such an enzyme. Enzymes that catalyze a reaction for generating a compound other than L-lysine by branching off from the biosynthetic pathway of L-lysine include homoserine dehydrogenase and lysine decarboxylase. Strains having decreased activities of the enzymes are described in WO95/23864 and WO 96/178930.

<2> Modification for Decreasing Acetyl-CoA Hydrolase Activity

The coryneform bacterium of the present invention has an ability to produce an L-amino acid generated by a biosynthetic pathway in which pyruvic acid is an intermediate as mentioned above and modified so that acetyl-CoA hydrolase (EC 3.1.2.1) activity is decreased.

The coryneform bacterium of the present invention may be obtained by modifying the above-mentioned coryneform bacterium which has an ability to produce L-amino acids generated by a biosynthetic pathway in which pyruvic acid is an intermediate so that acetyl-CoA hydrolase activity is decreased. When breeding the coryneform bacteria of the present invention, imparting L-amino acid-producing ability to the bacteria or modifying the bacteria so that acetyl-CoA hydrolase activity is descreased may be performed in any order.

"Acetyl-CoA hydrolase (ACH) activity" refers to the activity to catalyze production of acetic acid from acetyl-CoA and $H_2O$. "Modified so that acetyl-CoA hydrolase activity is decreased" means that acetyl-CoA hydrolase activity is lower than in non-modified strains, including a wild-type coryneform bacterium. The ACH activity is preferably decreased to 50% or less, more preferably 30% or less, still more preferably 10% or less per unit cell weight as compared to a non-modified strain. Herein, a wild-type coryneform bacterium that serves as a control includes, for example, Brevibacterium lactofermentum 2256 strain (ATCC 13869) or Corynebacterium glutamicum ATCC13032, and a non-modified strain includes Brevibacterium lactofermentum Δ1dh strain. The acetyl-CoA hydrolase activity can be measured according to the method of Gergely, J., et al., (Gergely, J., Hele, P. & Ramkrishnan, C. V. (1952) J. Biol. Chem. 198 p 323-334). "Decrease" includes when the activity has completely disappeared. It is preferable that the coryneform bacterium of the present invention has acetyl-CoA hydrolase activity which is less than that of a wild-type or non-modified strain and generates or produces L-amino acids more than a wild-type or non-modified strain.

Examples of ACH include a protein of the amino acid sequence shown in SEQ ID NO: 24, and a protein of the amino acid sequence of SEQ ID NO: 24 wherein one or more amino acids are replaced, deleted, inserted, or added at one or more positions, but maintains ACH activity. Although the number of "several" amino acid residues referred to herein may differ depending on positions in the three-dimensional structure or types of amino acid residues of the protein, it may be preferably 1 to 20, more preferably 1 to 10, particularly preferably 1 to 5. The ACH gene preferably encodes a protein having homology of not less than 80%, more preferably not less than 90%, even more preferably not less than 95%, particularly preferably not less than 97% to the amino acid sequence shown in SEQ ID NO: 24, while maintaining ACH activity. Substitution of amino acids in these ACH homologs is preferably a conservative substitution, including substitution of ser or thr for ala, substitution of gln, his or lys for arg, substitution of glu, gln, lys, his or asp for asn, substitution of asn, glu or gln for asp, substitution of ser or ala for cys, substitution of asn, glu, lys, his, asp or arg for gln, substitution of gly, asn, gln, lys or asp for glu, substitution of pro for gly, substitution of asn, lys, gln, arg or tyr for his, substitution of leu, met, val or phe for ile, substitution of ile, met, val or phe for leu, substitution of asn, glu, gln, his or arg for lys, substitution of ile, leu, val or phe for met, substitution of trp, tyr, met, ile or leu for phe, substitution of thr or ala for ser, substitution of ser or ala for thr, substitution of phe or tyr for trp, substitution of his, phe or trp for tyr and substitution of met, ile or leu for val.

"Modified so that acetyl-CoA hydrolase activity is decreased" includes when the number of molecules of acetyl-CoA hydrolase per cell decreases, and when the CoA hydrolase activity per molecule decreases. Specifically, these modifications may be achieved, for example, by disrupting a gene encoding acetyl-CoA hydrolase on a chromosome, or by modifying an expression regulatory sequence such as a promoter and/or a Shine-Dalgarno (SD) sequence. The acetyl-CoA hydrolase gene on a chromosome includes, for example, a DNA comprising nucleotides 1037 to 2542 of SEQ ID NO: 23. Furthermore, acetyl-CoA hydrolase gene include, for example, a DNA obtainable by using primers SEQ ID 7 and 8 in PCR. In addition, the chromosomal acetyl-CoA hydrolase gene may be a DNA that is able to hybridize with the nucleotides 1037 to 2542 of SEQ ID No. 23 or a probe that can be prepared from the nucleotides under stringent conditions so long as it encodes a protein having acetyl-CoA hydrolase activity. "Stringent conditions" refers to conditions under which so-called specific hybrids are formed and non-specific hybrids are not formed. Examples of such conditions include when washing is performed once, preferably two to three times at 60° C. and at a salt concentration corresponding to 1×SSC, 0.1% SDS, preferably 0.1×SSC, 0.1% SDS.

The acetyl-CoA hydrolase gene (hereinafter, referred to as the "ach gene") may be cloned by synthesizing synthetic oligonucleotides based on a nucleotide sequence of Corynebacterium glutamicum (for example, SEQ ID No. 23, NCgl2480 of GenBank Accession No. NC_003450 (a complementary strand from 2729376 to 2730884 of NC_003450)), and performing PCR using a chromosomal DNA of Corynebacterium glutamicum as a template. In addition, another nucleotide sequence derived from coryneform bacterium such as Brevibacterium lactofermentum is also available. Chromosomal DNA can be prepared from a coryneform bacterium as a DNA donor by, for example, the method of Saito and Miura (H. Saito and K. Miura, *Biochem. Biophys. Acta,* 72, 619 (1963), "Biotechnology Experiments Handbook", ed. by The Society for Biotechnology Japan, p. 97 to 98, Baifukan, 1992).

The ach gene thus prepared or a part thereof can be used for disrupting the chromosomal ach gene. In addition, the ach gene used for disrupting the chromosomal ach gene may also be a gene having homology sufficient to cause homologous recombination with the ach gene on the chromosome of a target coryneform bacterium (for example, a gene having nucleotides 1037 to 2542 of SEQ ID NO: 23). Herein, homology sufficient to cause homologous recombination is preferably 80% or more, more preferably 90% or more, still more preferably 95% or more, particularly preferably 97% or more. Furthermore, a DNA that can hybridize under stringent conditions with the above-mentioned gene may also be used for gene disruption.

The ach gene can be disrupted, for example, by preparing a "deletion-type ach gene" in which a partial sequence of the ach gene is deleted so that normally functioning acetyl-CoA hydrolase is not produced, transforming a coryneform bacterium with a DNA containing the deletion-type ach gene to cause recombination between the deletion-type ach gene and the ach gene on a chromosome. Such gene disruption by gene substitution utilizing homologous recombination is already established and includes a method that employs a linear DNA or a method that employs a plasmid containing temperature-sensitive replication origin (U.S. Pat. No. 6,303,383, or JP-A-05-007491). Gene disruption by gene substitution utilizing homologous recombination can also be performed by using a plasmid which is not replicable in coryneform bacteria. A plasmid which is not replicable in coryneform bacteria but is replicable in *Escherichia* bacteria is preferably used. Examples of such a plasmid include pHSG299 (Takara Bio) and pHSG399 (Takara Bio).

A chromosomal ach gene can be replaced with a deletion-type ach gene, for example, by homologous recombination using sacB (Schafer, A. et al., Gene 145 (1994) 69-73). The sacB gene encodes a levan sucrase and is used to efficiently select strains in which a chromosomal target gene is replaced by a mutant gene and the vector portion is cured from a chromosome.

At first, a recombinant plasmid is prepared by inserting a deletion-type (mutant) ach gene, sacB gene, and a selection marker such as a chloramphenicol-resistant gene into a plasmid containing a temperature-sensitive replication origin. The obtained plasmid is introduced into a host strain of coryneform bacterium. When levan sucrase is expressed in cells of coryneform bacterium, levan generated by conversion of sucrose is lethal for the bacterium and hence the bacterium cannot grow on sucrose-containing medium. Therefore, by culturing on a sucrose-containing plate, strains in which substitution occurs between the mutant ach gene in the plasmid and a chromosomal ach gene and from which the other portions of the plasmid are cured from the cell, can be selected.

Examples of the sacB gene include the following.

*Bacillus subillus*: sacB GenBank Accession Number X02730 (SEQ ID NO: 19)

*Bacillus amyloliqufaciens*: sacB GenBank Accession Number X52988

*Zymomonas mobilis*: sacB GenBank Accession Number L33402

*Bacillus stearothermophilus*: surB GenBank Accession Number U34874

*Lactobacillus sanfranciscensis*: frfA GenBank Accession Number AJ508391

*Acetobacter xylinus*: lsxA GenBank Accession Number AB034152

*Gluconacetobacter diazotrophicus*: lsdA GenBank Accession Number L41732

Transformation can be performed by conventional methods. For example, a method of treating recipient cells with calcium chloride so as to increase the permeability of DNA, which has been reported for *Escherichia coli* (Mandel, M. and Higa, A., J. Mol. Biol., 53, 159 (1970)), and a method of using competent cells prepared from growing cells to introduce a DNA, which has been reported for *Bacillus subtilis* (Duncan, C. H., Wilson, G. A. and Young, F. E., Gene, 1, 153 (1977)) can be employed. In addition to these methods, introducing a recombinant DNA into protoplast- or spheroplast-like recipient cells, which has been reported to be applicable to *Bacillus subtilis*, actinomycetes, and yeasts (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)), can be employed. In addition, transformation of Coryneform bacteria can also be performed by the electric pulse method (Sugimoto et al., JP2-207791A).

Examples of temperature-sensitive plasmids for coryneform bacteria include p48K and pSFKT2 (EP1038966), pHSC4 (France Patent Laid-open Publication No. 2667875, 1992 and JP5-7491A), pBS5T, and so forth. In coryneform bacteria, these plasmids can autonomously replicate at least at a temperature of 25° C., but cannot autonomously replicate at a temperature of 37° C. The AJ12571 strain harboring pHSC4 was deposited at the National Institute of Bioscience and Human Technology, Agency of Industrial Science and Technology, Ministry of International Trade and Industry (currently International Patent Organism Depositary, National Institute of Advanced Industrial Science and Technology at Tsukuba Central 6, 1-1, Higashi 1-chome, Tsukuba-shi, Ibaraki-ken 305-5466, Japan) on Aug. 26, 1991 under the provisions of the Budapest Treaty and given an accession number of FERM BP-3524.

The transformant strain is cultured at a temperature at which the temperature-sensitive replication origin does not function (e.g. 25° C.) to obtain a strain into which the plasmid has been introduced. Then, the transformant is cultured at a high temperature to cure the temperature-sensitive plasmid, and spread on a plate medium containing an antibiotic drug such as kanamycin. Although strains from which the plasmid is cured cannot grow on a plate containing such an antibiotic drug, a few strains in which the chromosomal ach gene is replaced with the mutant ach gene can grow and appear as colonies.

In a strain in which the recombinant DNA containing the mutant ach gene is integrated into the chromosomal DNA, the recombinant DNA causes recombination with the ach gene that originally existed on the chromosome, and the fusion genes of the chromosomal ach gene and the mutant ach gene are inserted into the chromosome so that the other portions of the recombinant DNA (vector segment, temperature sensitive replication origin and drug resistance marker) are present between the fusion genes. Then, in order to leave only the mutant ach gene on the chromosomal DNA, one copy of the ach gene is eliminated together with the vector segment (including the temperature-sensitive replication origin and the drug resistance marker) from the chromosomal DNA. In this case, the normal ach gene is left on the chromosomal DNA and the mutant ach gene is excised from the chromosomal DNA, or to the contrary, the mutant ach gene is left on the chromosomal DNA and the normal ach gene is excised from the chromosome DNA. Then, a strain in which only the mutant ach gene remains on the chromosome can be selected by using PCR, Southern hybridization, or the like.

Decreasing acetyl-CoA hydrolase activity may also be achieved by modifying an expression regulatory sequence such as a promoter, Shine-Dalgarno (SD) sequence, operator, terminator, and attenuator. The expression regulatory sequence on a chromosome may be identified by gene-analyzing software such as Genetix, by vectors for expression analysis such as promoter-searching vector, and by known information such as from the Genbank database. For example, examples of mutations that decrease acetyl-CoA hydrolase activity include a mutation which modifies a promoter region of acetyl-CoA hydrolase gene to be less potent and a mutation which disrupts a consensus sequence in a promoter region of acetyl-CoA hydrolase. Such mutations may be introduced by using temperature-sensitive plasmids or suicide vectors that are not capable of replicating in a host cell.

Decreasing acetyl-CoA hydrolase activity may also be achieved by introducing amino acid substitutions (mls-sense mutation) in a coding region of acetyl-CoA hydrolase gene on a chromosome, introducing a stop codon (nonsense mutation), introducing a frame shift mutation by which one or two nucleotides are added or deleted, or by deleting a part of the gene (*Journal of Biological Chemistry* 272:8611-8617 (1997)).

Examples of a method of decreasing acetyl-CoA hydrolase activity also include a method of treating coryneform bacteria with ultraviolet irradiation or with a typical mutagen, such as N-methyl-N'-nitro-N-nitrosoguanidine (NTG) and nitrous acid, to select strains having decreased acetyl-CoA hydrolase activity. ("Amino Acid Fermentation", Center for Academic Publications Japan Co., Ltd., 1st ed. published on May 30, 1986, p. 77 to 100).

Meanwhile, strains further modified so that glutamic acid dehydrogenase (hereinafter, referred to as "GDH") activity is enhanced are preferably used in the present invention.

To amplify the GDH activity in a coryneform bacterium which has L-amino acid-producing ability and has been modified to decrease ACH activity, a gene fragment encoding GDH is ligated to a vector that functions in coryneform bacteria, preferably to a multi-copy type vector to make a recombinant DNA, and the coryneform bacterium is transformed with the resulting DNA. As a result of the increase in the copy number of a gene that encodes GDH in the cells of the transformants, the GDH activity is amplified.

The gene encoding GDH may be derived from coryneform bacteria or may be derived from other organisms such as *Escherichia coli*.

The nucleotide sequence of the gene encoding GDH of coryneform bacteria (gdh gene) has already been identified (for example, SEQ ID NO: 25: *Molecular Microbiology* (1992) 6(3), 317-326 1999, a complementary strand of 2194739 . . . 2196082 of NC_003450), so that gdh gene can be obtained by PCR using primers designed based on the nucleotide sequence and a chromosomal DNA of coryneform bacteria as a template (PCR: polymerase chain reaction; White, T. J. et al.; Trends Genet. 5, 185 (1989)). Genes encoding GDH of other microorganisms may also be obtained in the same manner.

<3> Production of L-Amino Acids Using Coryneform Bacteria of the Present Invention L-amino acids generated using pyruvic acid as an intermediate can be produced efficiently by culturing the coryneform bacteria obtained as described above in a medium to produce and cause accumulation of such L-amino acids, and collecting such L-amino acids from the medium.

To produce such L-amino acids using the coryneform bacteria of the present invention, a culture can be performed by a conventional method with an ordinary medium containing a carbon source, a nitrogen source, inorganic salts, and trace amount of organic nutrients such as amino acids and vitamins if required. Either a synthetic or natural media can be used. The carbon and nitrogen sources used in the culture media may be of any kind so long as they can be utilized by the strain of the present invention.

Examples of carbon sources include sugars such as glucose, glycerol, fructose, sucrose, maltose, mannose, galactose, starch hydrolysates, and molasses. Furthermore, organic acids such as citric acid and malate, and alcohols such as ethanol can be used alone or in combination with other carbon sources.

Examples of nitrogen sources include ammonia, ammonia salts such as ammonium sulfate, ammonium carbonate, ammonium chloride, ammonium phosphate, and ammonium acetate, and nitrates.

Examples of organic nutrients which can be present in trace amounts include amino acids, vitamins, fatty acids, and nucleic acids, and peptone, casamino acids, yeast extracts, and soybean protein hydrolysate containing these nutrients may also be used. In the case where nutrient-auxotrophic mutant strains that require amino acids and the like for growth are used, it is preferable that the required nutrients are supplemented.

Examples of the inorganic salts include phosphates, magnesium salts, calcium salts, iron salts, and manganese salts.

Culture is performed under aerobic conditions at a fermentation temperature of 20 to 45° C., while adjusting the pH to between 5 and 9. If the pH decreases during the culture, calcium carbonate or alkali such as ammonia gas may be added to the medium for neutralization. Culturing for about 10 to 120 hours results in the accumulation of considerable amounts of L-amino acids.

L-amino acids are collected from the medium after completion of the culture by a known recovery method. For example, after removal of the cells from the culture solution, the L-amino acids are collected by concentration and crystallization.

EXAMPLES

Hereinafter, the present invention is explained more specifically by way of the following non-limiting examples.

Example 1

<1> Construction of the Disruption Vector Carrying the sacB Gene (A) Construction of pBS3

A sacB gene (SEQ ID NO: 19) was obtained by PCR using the chromosomal DNA of *Bacillus subtilis* as a template and oligonucleotides of SEQ ID NOS: 1 and 2 as primers. The PCR was performed using LA taq (manufactured by TaKaRa) as follows: one cycle of heat retention at 94° C. for 5 minutes; and 25 cycles of denaturing at 94° C. for 30 seconds, annealing at 49° C. for 30 seconds, and elongation at 72° C. for 2 minutes. The PCR product was purified by a conventional method, and then digested with BglII and BamHI and blunt-ended. The fragment was inserted into pHSG299 which had been digested with AvaII and blunt-ended. This DNA was used to transform competent cells of *Escherichia coli* JM109 (manufactured by TAKARA BIO INC.). Then, the transformed bacterial cells were spread on LB agar medium containing 25 µg/ml Kanamycin (hereinafter, abbreviated as "Km"), and incubated for one night. Thereafter, single colonies were isolated as transformants. Plasmids were extracted from the obtained transformants and the plasmid which had an insert of the objective PCR product was named pBS3. FIG. 1 shows the procedure of construction of pBS3.

(B) Construction of pBS4S

The SmaI recognition site in the kanamycin-resistant gene on pBS3 was modified by nucleotide substitution using cross-over PCR without causing amino acid substitution so that pBS3 is not cut by SmaI endnuclease. First, PCR was performed using pBS3 as a template and synthetic DNAs of SEQ ID NOS: 3 and 4 as primers, to thereby obtain an N-terminal fragment of the kanamycin-resistant gene. On the other hand, to obtain a C-terminal fragment of the kanamycin-resistant gene, PCR was performed using pBS3 as a template and synthetic DNAs of SEQ ID NOS: 5 and 6 as primers. PCR was performed using Pyrobest DNA Polymerase (manufactured by TAKARA BIO INC.) as follows: one cycle of heat retention at 98° C. for 5 minutes; and 25 cycles of denaturing at 98° C. for 10 seconds, annealing at 57° C. for 30 seconds, and elongation at 72° C. for 1 minute, to obtain the objective PCR product. SEQ ID NOS: 4 and 5 are partially complementary to each other and do not contain the SmaI recognition site. Then, to obtain a full-length fragment of the mutant kanamycin-resistant gene without the SmaI recognition site, the above-mentioned N-terminal and C-terminal gene products were mixed together in substantially equimolar amounts. PCR was performed using the gene products as a template and synthetic DNAs of SEQ ID NOS: 3 and 6 as primers to obtain a SmaI site-modified kanamycin-resistant gene fragment. The PCR was performed using Pyrobest DNA Polymerase (manufactured by TAKARA BIO INC.) as follows: one cycle of heat retention at 98° C. for 5 minutes; and 25 cycles of denaturing at 98° C. for 10 seconds, annealing at 57° C. for 30 seconds, and elongation at 72° C. for 1.5 minutes, to thereby obtain the objective PCR product.

Figure 2:
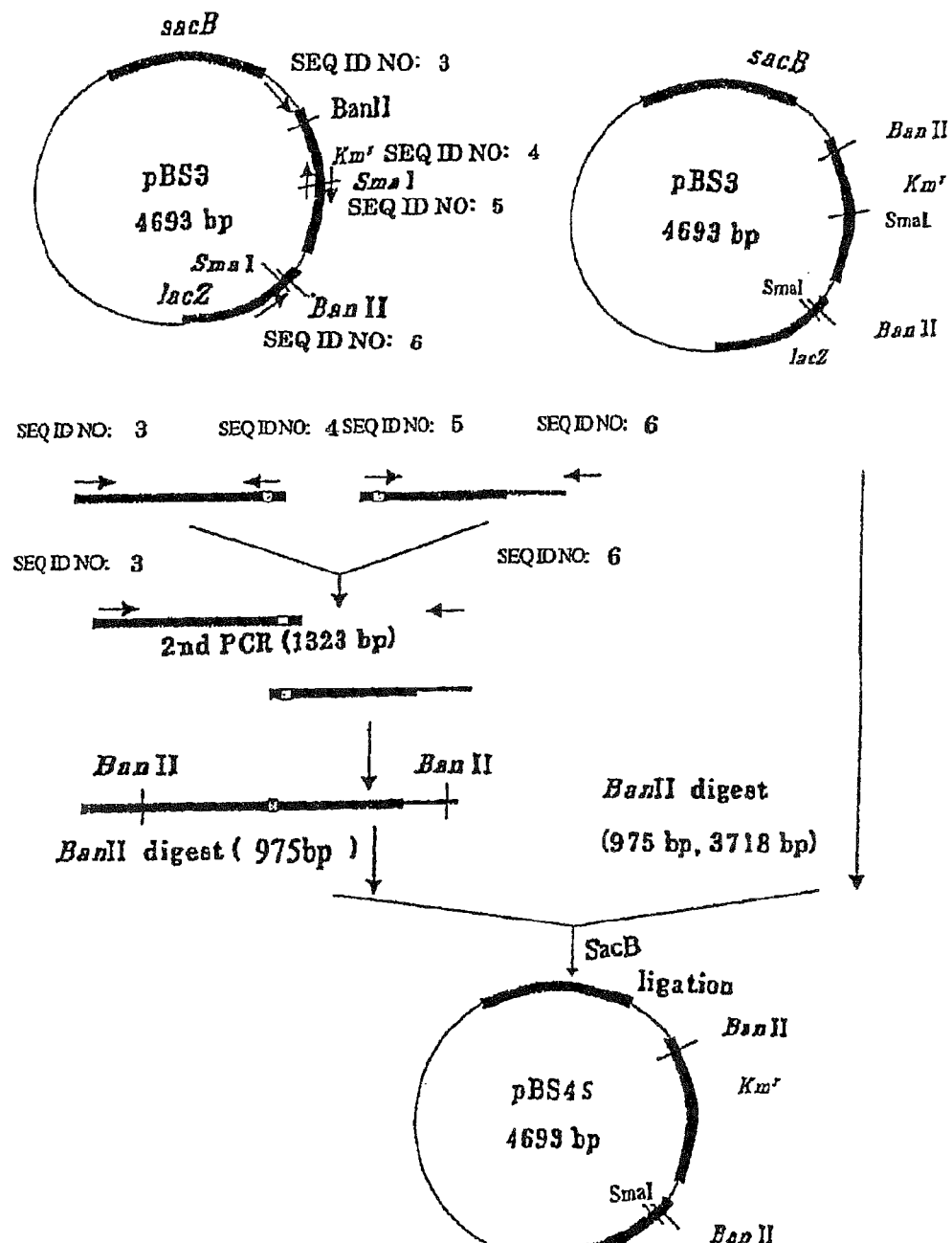
FIG. 2 is a scheme showing the procedure for constructing plasmid pBS4.

The PCR product was purified by a conventional method, and then digested with BanII and then inserted into the above-described BanII recognition site of pBS3. The resulting plasmid was used to transform competent cells of *Escherichia coli* JM109 (available from Takara Bio). That is, the transformed bacterial cells were spread on LB agar medium containing 25 µg/ml of kanamycin, and incubated for one night. Thereafter, colonies that appeared were selected as transformants. Plasmids were isolated from the obtained transformants and the plasmid having an insert of the objective PCR product was named pBS4S. FIG. 2 shows the procedure for constructing pBS4S.

(C) Construction of pBS5T

Figure 3:
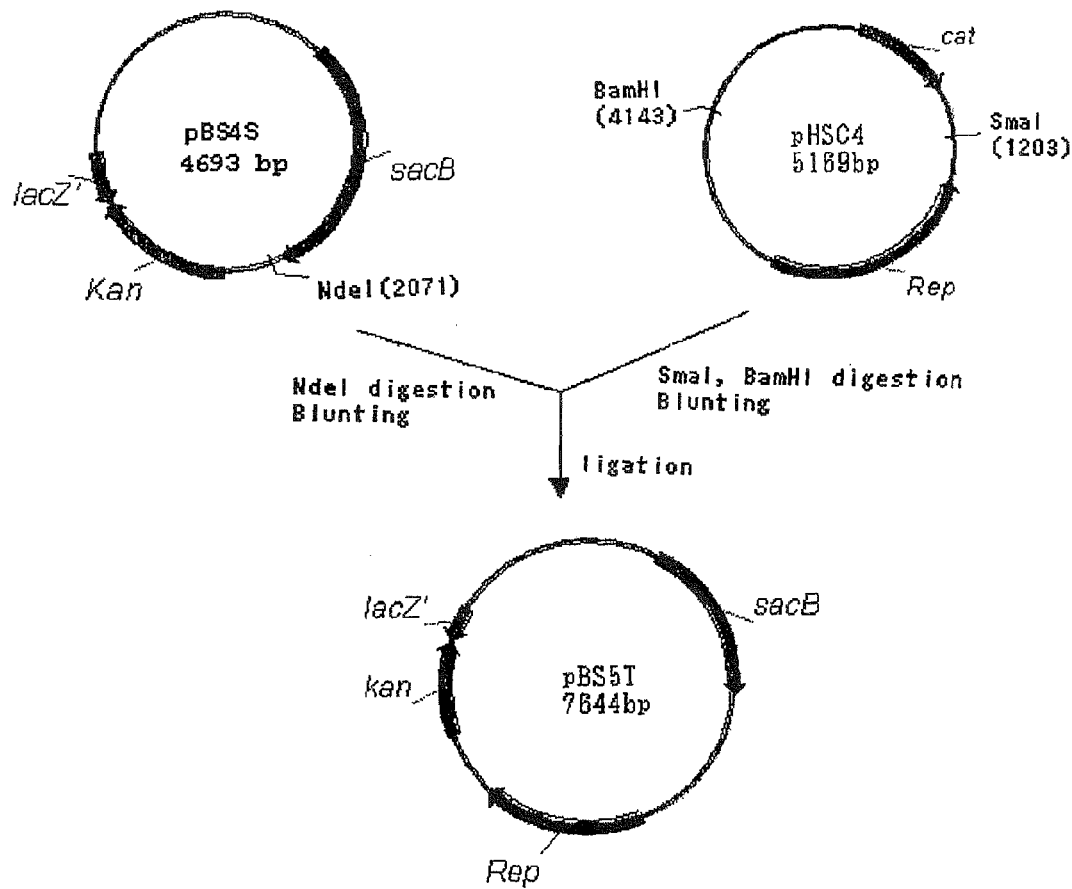
FIG. 3 is a scheme showing the procedure for constructing plasmid pBS5T.

A temperature-sensitive replication origin in coryneform bacterium was excised from pHSC4 (JP-A-5-7491) by digesting it with BamHI and SmaI and blunt-ending, and inserted into the blunt-ended NdeI site of pBS4S. Using this DNA, competent cells of *Escherichia coli* JM109 (manufactured by TAKARA BIO INC.) were transformed and spread on an LB agar medium containing 25 µg/ml Km, followed by culturing overnight. Then, single colonies were isolated as transformants. Plasmids were extracted from the transformants and a plasmid having an insert of the objective PCR product was named pBS5T. FIG. 3 shows a construction procedure of pBS5T.

Example 2

<Construction of ldh-Disrupted Strain>

(A) Cloning of a Fragment to Disrupt the Lactate Dehydrogenase Gene

A gene fragment containing lactate dehydrogenase (hereinafter, abbreviated as "ldh gene") derived from *Brevibacterium lactofermentum* 2256 strain having the ORF deleted was obtained by cross-over PCR using synthetic DNAs designed based on the nucleotide sequence of the ldh gene of the *Corynebacterium glutamicum* ATCC13032 strain (SEQ ID NO: 21: GenBank Database Accession No. NC_003450), as primers. Specifically, PCR was performed by a conventional method using a chromosomal DNA of *Brevibacterium lactofermentum* 2256 strain as a template and the synthetic DNAs of SEQ ID NOS: 7 and 8 as primers to obtain the N-terminal fragment of the ldh gene. On the other hand, to obtain a C-terminal fragment of the ldh gene, PCR was performed by a conventional method using the chromosomal DNA of *Brevibacterium lactofermentum* 2256 strain as a template and synthetic DNAs of SEQ ID NOS: 9 and 10 as primers. SEQ ID NOS: 8 and 9 were complementary to each other and designed to result in deletion of the entire sequence of the ORF of the ldh gene.

Figure 4:
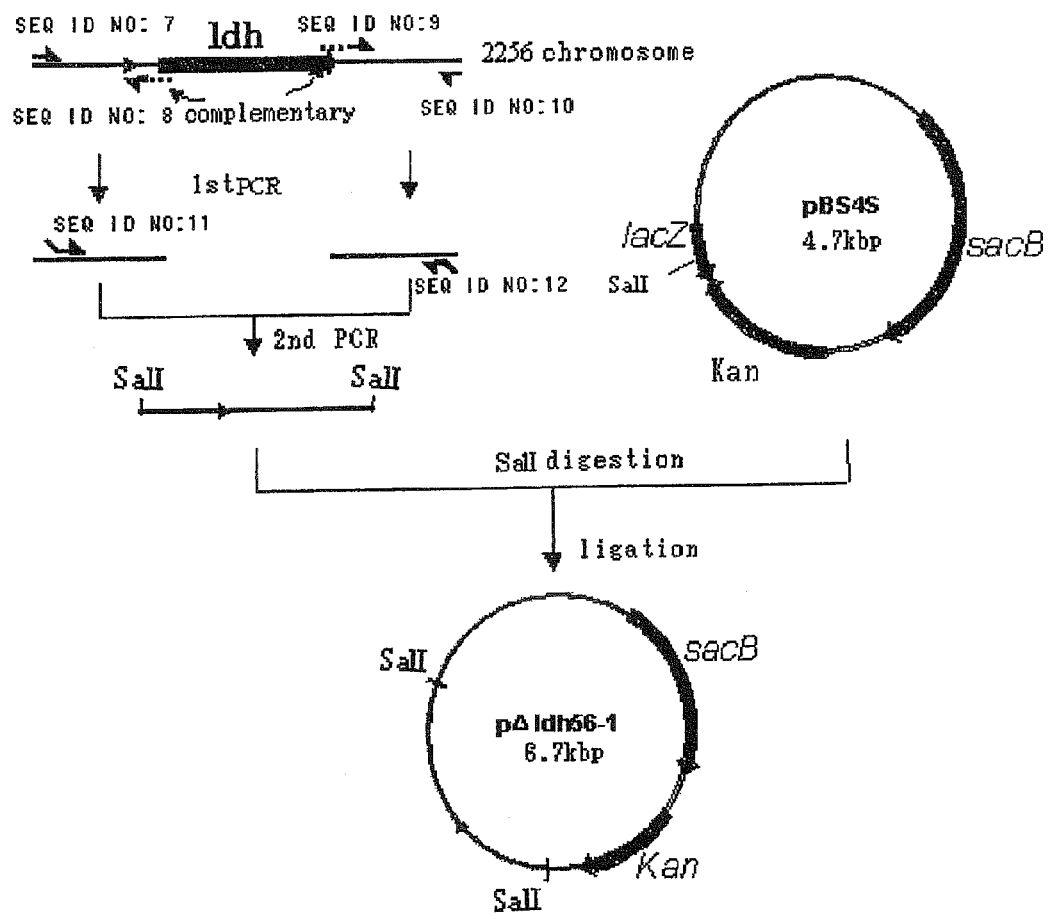
FIG. 4 is a scheme showing the procedure for constructing plasmid pΔldh56-1.

Then, to obtain an ldh gene fragment having an internal sequence deleted, the N-terminal and C-terminal gene products of ldh were mixed in substantially equimolar amounts and PCR was performed by a conventional method using the mixture as a template and the synthetic DNAs of SEQ ID NOS: 11 and 12 as primers. After purifying the PCR product in a conventional manner, the PCR products were digested with SalI. Thereafter, the PCR product was inserted into the SalI site of the above-mentioned pBS4S. With this DNA, competent cells of *Escherichia coli* (manufactured by TAKARA BIO INC.) were transformed and spread over an LB agar medium containing 100 µM IPTG, 40 µg/ml X-Gal, and 25 µg/ml Km, and followed by culturing overnight. Thereafter, single colonies were isolated as transformants. Plasmids were extracted from the transformants, and a plasmid having the insert of the objective PCR product was named pΔldh56-1. FIG. 4 shows a construction procedure of the plasmid.

(B) Preparation of ldh-Disrupted Strain

Since pΔldh56-1 prepared as described in (A) does not contain a region that allows for autonomous replication in coryneform bacteria, when coryneform bacteria are transformed with the plasmid, transformant strains having the plasmid incorporated into the chromosome by homologous recombination appear at extremely low frequently. Thus, *Brevibacterium lactofermentum* 2256 strain was transformed using a solution containing a high concentration of plasmid pΔldh56-1 by the electric pulse method, and then spread on CM-Dex agar medium containing 25 µg/ml kanamycin (5 g/L glucose, 10 g/L polypeptone, 10 g/L yeast extract, 1 g/L KH$_2$PO$_4$, 0.4 g/L MgSO$_4$.7H$_2$O, 0.01 g/L FeSO$_4$.7H$_2$O, 0.01 g/L MnSO$_4$.7H$_2$O, 3 g/L urea, 1.2 g/L soybean hydrolysates, and pH 7.5 (KOH)), and cultured at 31.5° C. for about 30 hours. Colonies that appeared on this medium were strains in which homologous recombination had occurred between the ldh gene fragment of the plasmid and the ldh gene on the chromosome of *Brevibacterium lactofermentum* 2256 strain, and the kanamycin-resistant gene and the SacB gene derived from the plasmid were inserted into the chromosome.

Then, these first recombinants were cultured in CM-Dex liquid medium containing no kanamaycin at 31.5° C. for one night. After appropriate dilution, the recombinants were spread on 10% sucrose-containing Dex-S10 agar medium (10 g/L sucrose, 10 g/L polypeptone, 10 g/L yeast extract, 1 g/L KH$_2$PO$_4$, 0.4 g/L MgSO$_4$.7H$_2$O, 0.01 g/L FeSO$_4$.7H$_2$O, 0.01 g/L MnSO$_4$.4H$_2$O, 3 g/L urea, 1.2 g/L soybean hydrolysates, 10 µg/L biotin, and pH 7.5 (KOH)) and cultured at 31.5° C. for about 30 hours. As a result, about 50 strains from which the sacB gene was cured by a second recombination and which had become sucrose-insensitive were obtained.

The strains thus obtained include strains in which the chromosomal ldh gene was replaced by a mutant ldh gene derived from pΔldh56-1, and strains in which the chromosomal wild-type ldh gene remained. Whether the ldh gene was a mutant or a wild-type was easily checked by subjecting the cells obtained by culturing on Dex-S10 agar medium to direct PCR. Using primers (SEQ ID NOS: 7 and 10) for PCR amplification to analyze the ldh gene, a strain with a PCR product that is smaller than the wild-type ldh gene which has been amplified using the chromosomal DNA of the wild-type 2256 strain as a template was selected as a ldh-disrupted strain, and named 2256Δ(ldh) strain. This strain was used as a parent strain for preparing the following ach gene-disrupted strain.

When fermentation is performed under anaerobic conditions, a considerable amount of lacetic acid accumulates as a by-product, so it is preferable that lactate dehydrogenase activity is deficient. (JP11-206385; J Mol Microbiol Biotechnol. 2004; 7(4):182-96.) However, L-glutamic acid is usually produced under aerobic conditions which do not allow lactate dehydrogenase to function, and it is not necessary to disrupt the ldh gene in acetyl-CoA hydrolase gene-disrupted strains for L-glutamic acid production.

Example 3

<Construction of an Acetyl-CoA Hydrolase Gene-Disrupted Strain>

(A) Cloning of a Fragment for Disrupting Acetyl-CoA Hydrolase Gene

Figure 5:
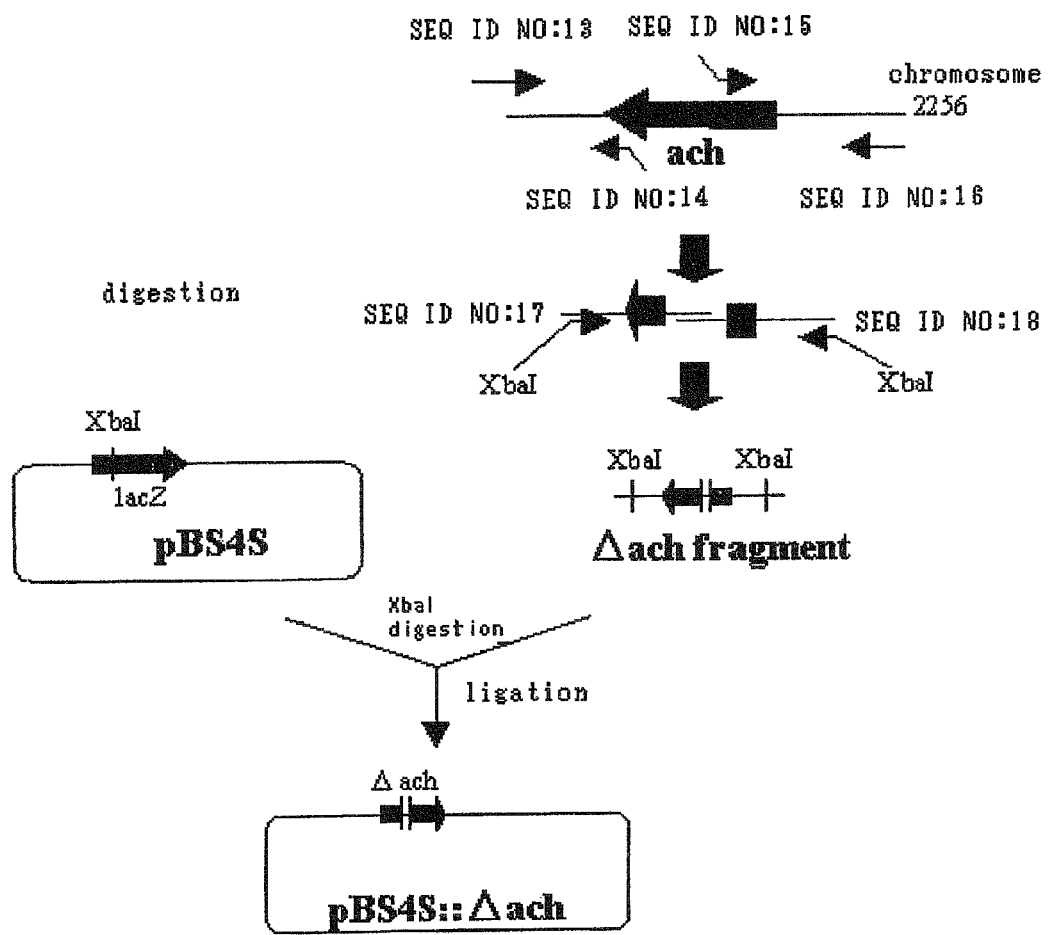
FIG. 5 is a scheme showing the procedure for constructing plasmid pBS4S::Δach.

A gene fragment containing acetyl-CoA hydrolase gene (hereinafter, the gene is referred to as "ach") derived from *Brevibacterium lactofermentum* 2256 strain having the ORF deleted was obtained by cross-over PCR using synthetic DNAs designed based on the nucleotide sequence of the gene of Corynebacterium glutamicum ATCC13032 (SEQ ID NO: 23: GenBank Database Accession No. NC_003450). Specifically, PCR was performed by a conventional method using the chromosomal DNA of *Brevibacterium lactofermentum* 2256 strain as a template and the synthetic DNAs of SEQ ID NOS: 13 and 14 as primers to obtain the C-terminal fragment of the ach gene. Alternatively, to obtain an N-terminal fragment, PCR was performed by a conventional method using the chromosomal DNA of *Brevibacterium lactofermentum* 2256 strain as a template and synthetic DNAs of SEQ ID NOS: 15 and 16 as primers. SEQ ID NOS: 14 and 15 were partially complementary to each other. A PCR reaction was performed using KOD-plus (manufactured by TOYOBO Co., LTD.). After performing 1 cycle of retention at 94° C. for 2 minutes, the following was repeated for 30 cycles: a cycle of denaturing at 94° C. for 10 seconds, annealing at 55° C. for 30 seconds, and elongation at 68° C. for 50 seconds. Then, to obtain an ach gene fragment having an internal sequence deleted, the N-terminal fragment and C-terminal fragment of the ach gene were mixed together in substantially equimolar amounts. PCR was performed by a conventional method using the mixture as a template and the synthetic DNAs of SEQ ID NOS: 17 and 18 as primers. A PCR reaction was performed using KOD-plus (manufactured by TOYOBO Co., LTD.). After performing 1 cycle of retention at 94° C. for 2 minutes, the following cycle was repeated for 30 cycles: denaturing at 94° C. for 10 seconds, annealing at 55° C. for 30 seconds, and elongation at 68° C. for 90 seconds. After purification of the amplified PCR product by a conventional manner, the PCR products were digested with XbaI and inserted into the XbaI site of the pBS4S constructed in the above example 1 (B). With the resulting DNA, competent cells of *Escherichia coli* JM109 (manufactured by TAKARA BIO INC.) were transformed and spread on an LB agar medium containing 100 µM IPTG, 40 µg/ml X-Gal, and 25 µg/ml Km, followed by culturing for one night. Thereafter, single white colonies were isolated as transformants. Plasmids were extracted from the transformants and one having an insert of the objective PCR product was named pBS4S::Δach. FIG. 5 shows a procedure of constructing pBS4S::Δach.

(B) Preparation of ach-Disrupted Strain

Since pBS4S::Δach prepared in the above (A) does not contain a region that enables autonomous replication in cells of coryneform bacteria, when coryneform bacteria are transformed with the plasmid, strains with the plasmid incorporated into its chromosome by homologous recombination appear as transformants at extremely low frequently. Thus, *Brevibacterium lactofermentum* 2256 Δ(ldh) strain was transformed using a solution containing a high concentration of plasmid pBS4S::Δach by the electric pulse method and spread on CM-Dex agar medium containing 25 µg/ml kanamycin, and cultured at 31.5° C. for about 30 hours. Strains that appeared on this medium were strains in which homologous recombination occurred between the deletion-type ach gene fragment of the plasmid and the ach gene on chromosome of *Brevibacterium lactofermentum* 2256 Δ(ldh) strain, and in which the kanamycin-resistant gene and the SacB gene derived from the plasmid were inserted into the chromosome.

Then, these first recombinants were cultured in a CM-Dex liquid medium not containing kanamycin at 31.5° C. for one night. After appropriate dilution, the recombinants were spread on a 10% sucrose-containing Dex-S10 agar medium, and cultured at 31.5° C. for about 30 hours. As a result, about 50 strains from which the SacB gene was cured from chromosome by a second recombination and which had become sucrose-insensitive were obtained.

The strains thus obtained include those strains in which the chromosomal ach gene was replaced by a mutant-type derived from pBS4S::Δach and those strains in which the chromosomal wild-type ach gene remained. Whether the ach gene was a mutant-type or a wild-type was easily confirmed by subjecting the cells obtained by culturing on Dex-S10 agar medium to direct PCR. Upon analysis of the ach gene using primers (SEQ ID NOS: 13 and 16), a DNA fragment of 2.9 kb for a wild-type ach gene and a DNA fragment of 1.4 kb for a mutant-type ach gene were amplified. As a result of the analysis of sucrose-insensitive strains by the above method, strains containing only a mutant type ach gene were selected, and the ach-disrupted strain obtained from 2256 Δ(ldh) strain was named 2256 Δ(ldh, ach) strain.

Example 4

<Production of L-Glutamic Acid by ach-Disrupted Strain>

(1) Evaluation of L-Glutamic Acid-Producing Ability of ach-Disrupted Strain

*Brevibacterium lactofermentum* 2256 Δ(ldh) strain and 2256 Δ(ldh, ach) strain were cultured for L-glutamic acid production in an S-type jar as follows. One loop each of 2256 Δ(ldh) strain and 2256 Δ(ldh, ach) strain which had been cultured on a CMDex agar plate was inoculated into 300 ml of seed medium (60 g of glucose, 1.54 g of H$_3$PO$_4$, 1.45 g of KOH, 0.9 g of MgSO$_4$.7H$_2$O, 0.01 g of FeSO$_4$.7H$_2$O, 670 µg of VB1.HCl, 40 µg of Biotin, 1.54 g of soybean hydrolysates, 0.28 g of DL-methionine, 0.1 ml of AZ-20R per 1 liter of purified water (adjusted to pH 7.2 with ammonia water)), and cultured with aeration at 1/1 vvm until residual sugar was completely consumed while controlling the pH at 7.2 ($NH_3$), temperature at 31.5° C., and PL>0.

30 ml of the culture broth was inoculated into 270 ml of main culture medium (80 g of glucose, 3.46 g of $KH_2PO_4$, 1 g of $MgSO_4.7H_2O$, 0.01 g of $FeSO_4.7H_2O$, 0.01 g of $MnSO_4.4-5H_2O$, 230 µg of VB1.HCl, 0.35 g of soybean hydrolysates, and 0.2 ml of AZ-20R per 1 liter of purified water (adjusted to pH 7.3 with ammonia)) and cultured with aeration at 1/1 vvm while controlling temperature at 31.5° C., pH at 7.3, and PL>0. Before the residual sugar was completely consumed, 70 to 80 ml of a feed solution composed of 500 g of glucose and 0.2 ml of AZ-20R per 1 L of purified water was added and the culture was continued until the residual sugar was completely consumed.

After completion of the culture, the amount of L-glutamic acid (Glu) which had accumulated in the culture broth was analyzed in a Biotech Analyzer AS210 (manufactured by Asahi Kasei Corporation.) after appropriate dilution of the culture broth. Table 1 shows the results.

TABLE 1

Production of L-glutamic acid by an ach-deficient strain

| Strain | OD620 nm (×101) | Sugar consumed (g) | Glu (g/L) | Glu Yield (%) | α-KG (g/L) |
|---|---|---|---|---|---|
| 2256 Δ (ldh) | 0.720 | 60.1 | 87.8 | 51.8 | 2.66 |
| 2256 Δ (ldh, ach) | 0.629 | 63.6 | 93.6 | 53.9 | 8.45 |

2256 Δ(ldh, ach) strain showed about a 2% improvement in yield as compared with the 2256 Δ(ldh) strain (the parent strain). Furthermore, the amount of α-ketoglutarate (α-KG), which is a precursor of L-glutamic acid, which had accumulated improved about three times. The results showed that elimination or decrease of ACH activity is effective in the production of L-glutamic acid.

Example 5

<Production of L-Alanine and L-Valine by ach-Deficient Strain>

(1) Evaluation of Culture of ach-Deficient Strain

*Brevibacterium lactofermentum* 2256 Δ(ldh) strain and 2256 Δ(ldh, ach) strain were cultured for L-alanine and L-valine production in an S-type jar as follows. One loop each of the 2256 Δ(ldh) strain and the 2256 Δ(ldh, ach) strain, which had been cultured on a CMDex agar plate, was inoculated into 300 ml of a seed medium (60 g of glucose, 1.54 g of $H_3PO_4$, 1.45 g of KOH, 0.9 g of $MgSO_4.7H_2O$, 0.01 g of $FeSO_4.7H_2O$, 670 µg of VB1.HCl, 40 µg of biotin, 1.54 g of soybean hydrolysates, 0.28 g of DL-methionine, 0.1 ml of AZ-20R per 1 liter of purified water (adjusted to pH 7.2 with ammonia water)), and cultured with aeration at 1/1 vvm until residual sugar was completely consumed, while controlling the pH at 7.2 with ammonia, temperature at 31.5° C., and PL>0.

30 ml of the culture broth was inoculated into 270 ml of main culture medium (80 g of glucose, 3.46 g of $KH_2PO_4$, 1 g of $MgSO_4.7H_2O$, 0.01 g of $FeSO_4.7H_2O$, 0.01 g of $MnSO_4.4-5H_2O$, 230 µg of VB1.HCl, 0.35 g of soybean hydrolysates, and 0.2 ml of AZ-20R per 1 liter of purified water (adjusted to pH 7.3 with ammonia)) and cultured with aeration at 1/1 vvm while controlling the temperature at 31.5° C., pH at 7.3, and PL>0. Before the residual sugar was completely consumed, 70 to 80 ml of feed solution composed of 500 g of glucose and 0.2 ml of AZ-20R per 1 L of purified water was added and culture was continued until the residual sugar was completely consumed.

After completion of culture, the amount of L-alanine (Ala) and L-valine (Val) which had accumulated in the culture broth was analyzed with Amino Acid Analyzer L8500 (manufactured by Hitachi, Ltd.) after appropriate dilution of the culture broth. Table 2 shows the results.

TABLE 2

Production of Ala, Val by ach-deficient strain

| Strain | OD620 nm (×101) | Ala (g/L) | Val (g/L) |
|---|---|---|---|
| 2256 Δldh | 0.72 | 1.149 | 0.052 |
| 2256 ΔldhΔach | 0.629 | 2.533 | 0.214 |

2256 Δ(ldh, ach) showed about 2.2 times improvement of the amount of accumulated L-alanine, and about four times improvement of the amount of accumulated L-valine. The results showed that elimination or decrease of ACH activity is effective in the production of L-valine and L-alanine.

INDUSTRIAL APPLICABILITY

According to the present invention, the fermentation yield of L-amino acids generated by biosynthetic pathway using pyruvic acid as an intermediate is improved.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing one or more L-amino acids comprising:
   A) culturing a *Coryneform glutamicum* bacterium having the ability to produce an L-amino acid in a medium; and
   B) collecting the one or more L-amino acids from the medium;
   wherein said bacterium is modified so that acetyl-CoA hydrolase activity is decreased by disrupting a chromosomal acetyl-CoA hydrolase gene;
   and wherein the one or more L-amino acids is/are generated via a biosynthetic pathway in which pyruvic acid is an intermediate,
   and wherein said acetyl-CoA hydrolase is selected from the group consisting of:
   (A) a protein comprising the amino acid sequence shown in SEQ ID NO: 24; and
   (B) a protein comprising the amino acid sequence shown in SEQ ID NO: 24, whereby one to five amino acids in said amino acid sequence are substituted, deleted, inserted, or added.

2. The method according to claim 1, wherein said L-amino acids are selected from the group consisting of L-glutamic acid, L-arginine, L-glutamine, L-proline, L-alanine, L-valine, L-lysine, and combinations thereof.

3. The method according to claim 1, wherein said acetyl-CoA hydrolase gene is selected from the group consisting of:
   (a) a gene comprising nucleotides 1037 to 2542 of SEQ ID NO: 23; and
   (b) a DNA that is able to hybridize under stringent conditions to a polynucleotide comprising nucleotides 1037 to 2542 of SEQ ID NO: 23, and wherein said DNA encodes a protein having acetyl-CoA hydrolase activity, and wherein said stringent conditions comprise washing at 60° C. and at a salt concentration corresponding to 0.1× SSC, 0.1% SDS.

4. The method according to claim 1, wherein said bacterium is further modified to increase glutamate dehydrogenase activity by a method selected from the group consisting of:
   a) transformation with a plasmid comprising a gene encoding glutamate dehydrogenase;
   b) integrating a gene encoding glutamate dehydrogenase into the chromosome of said bacterium by homologous recombination, conjugation, or transposition;
   c) substituting a native promoter of a gene encoding glutamate dehydrogenase with a strong promoter; and
   d) combinations thereof.

5. The method according to claim 2, wherein said acetyl-CoA hydrolase gene is selected from the group consisting of:
   (a) a gene comprising nucleotides 1037 to 2542 of SEQ ID NO: 23; and
   (b) a DNA that is able to hybridize under stringent conditions to a polynucleotide comprising nucleotides 1037 to 2542 of SEQ ID NO: 23, and wherein said DNA encodes a protein having acetyl-CoA hydrolase activity, and wherein said stringent conditions comprise washing at 60° C. and at a salt concentration corresponding to 0.1× SSC, 0.1% SDS.

6. The method according to claim 2, wherein said bacterium is further modified to increase glutamate dehydrogenase activity by a method selected from the group consisting of:
   a) transformation with a plasmid comprising a gene encoding glutamate dehydrogenase;
   b) integrating a gene encoding glutamate dehydrogenase into the chromosome of said bacterium by homologous recombination, conjugation, or transposition;
   c) substituting a native promoter of a gene encoding glutamate dehydrogenase with a strong promoter; and
   d) combinations thereof.

* * * * *